(12) United States Patent
Sun et al.

(10) Patent No.: US 8,404,849 B2
(45) Date of Patent: Mar. 26, 2013

(54) PROCESSES FOR PRODUCING MODULATORS OF CYSTIC FIBROSIS TRANSMEMBRANE CONDUCTANCE REGULATOR

(75) Inventors: Lifang Sun, La Mesa, CA (US); Khisal Ahmed Alvi, San Diego, CA (US); Caroline Joyce Decker, Encinitas, CA (US); Yongmin Li, San Diego, CA (US)

(73) Assignee: Vertex Pharmaceuticals, Cambridge, MA (US)

( * ) Notice: Subject to any disclaimer, the term of this patent is extended or adjusted under 35 U.S.C. 154(b) by 0 days.

(21) Appl. No.: 13/112,868

(22) Filed: May 20, 2011

(65) Prior Publication Data

US 2011/0288121 A1 Nov. 24, 2011

Related U.S. Application Data

(60) Provisional application No. 61/346,781, filed on May 20, 2010, provisional application No. 61/379,614, filed on Sep. 2, 2010.

(51) Int. Cl.
*C07D 215/38* (2006.01)
(52) U.S. Cl. .......................... 546/126; 546/159
(58) Field of Classification Search .................. 546/126, 546/159; 514/304
See application file for complete search history.

(56) References Cited

U.S. PATENT DOCUMENTS

2011/0123449 A1* 5/2011 Zhang et al. .................. 424/9.1
2011/0124869 A1* 5/2011 Ambhaikar et al. .......... 546/156
2011/0257223 A1* 10/2011 Goor et al. .................... 514/304

FOREIGN PATENT DOCUMENTS

WO 2006/002421 A2 1/2006
WO 2010/048526 A2 4/2010
WO 2010048526 * 4/2010

OTHER PUBLICATIONS

Glieder, A., et al., "Laboratory evolution of a soluble, self-sufficient, highly active alkane hydroxylase," Nature Biotechnology, Nature Publishing Group, New York, NY, US, (Nov. 2002), vol. 20, No. 11, pp. 1135-1139, XP002615203.
Sun, Lifang, et al., "Effect of Organic Solvents on BM3-P450 Biotransformation," Drug Metabolism Reviews, (Aug. 2010), vol. 42, No. Suppl. 1, pp. 83-84, XP009150135.
Van Vugt-Lussenburg, Barbara M., et al., "Identification of critical residues in novel drug metabolizing mutants of cytochrome P450 BM3 using random mutagenesis," Journal of Medicinal Chemistry, (Feb. 2007), vol. 50, No. 3, pp. 455-461, XP002649499.
Zhang, Z., et al., "The substrate specificity of cytochrome P450cam.," Bioorganic & Medicinal Chemistry, (Sep. 1998), vol. 6, No. 9, pp. 1501-1508, XP002649498.
International Search Report for PCT/US2011/037420, dated Jul. 14, 2011.
Olivo, Horacio F., et al., "Microbial C-hydroxylation and B-4-O-methylglucosidation of methyl-benzamide 7-azanorbornane ethers with *Beauveria bassiana*," Journal or Molecular Catalysis B: Enzymatic, vol. 21, 2003, pp. 97-105.
Reinen, Jelle, et al., "Efficient Screening of Cytochrome P450 BM3 Mutants for Their Metabolic Activity and Diversity toward a Wide Set of Drug-like Molecules in Chemical Space," Drug Metabolism and Disposition, vol. 39, No. 9, 2011, pp. 1568-1576.
Van Vugt-Lussenburg, Barbara M.A., et al., "Evaluation of alkoxyresorufins as fluorescent substrates for cytochrome P450 BM3 and site-directed mutants," Analytical Biochemistry, vol. 341, 2005, pp. 148-155.

* cited by examiner

*Primary Examiner* — D M Seaman
(74) *Attorney, Agent, or Firm* — Honigman Miller Schwartz and Cohn LLP; Christopher C. Forbes; Jonathan P. O'Brien

(57) ABSTRACT

The present invention relates to the process for producing modulators of cystic fibrosis transmembrane conductance regulator (CFTR).

15 Claims, No Drawings

PROCESSES FOR PRODUCING MODULATORS OF CYSTIC FIBROSIS TRANSMEMBRANE CONDUCTANCE REGULATOR

PRIORITY CLAIM

This application claims priority to U.S. Provisional application Ser. No. 61/346,781, filed on May 20, 2010; and U.S. Provisional application Ser. No. 61/379,614, filed on Sep. 2, 2010. The entire contents of both priority documents are incorporated by reference herein.

FIELD OF THE INVENTION

The present invention relates to the process for producing modulators of cystic fibrosis transmembrane conductance regulator (CFTR).

BACKGROUND

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the cystic fibrosis transmembrane conductance regulator (CFTR) gene that encodes an epithelial chloride ion channel responsible for aiding in the regulation of salt and water absorption and secretion in various tissues. Small molecule drugs, known as potentiators that increase the probability of CFTR channel opening, represent one potential therapeutic strategy to treat CF.

Specifically, CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 1000 disease causing mutations in the CF gene have been identified (http://www.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and $Cl^-$ ion channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases.

Accordingly, there is a need for compounds that modulate CFTR. Specifically, there is a need for compounds of Formula I for the treatment of CFTR mediated diseases. There is also a need for processes that produce compounds that modulate CFTR.

SUMMARY OF THE INVENTION

In general, the invention relates to processes for producing the compounds of Formula I:

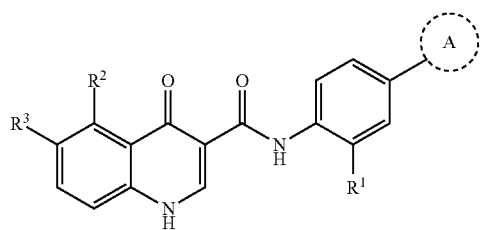

or pharmaceutically acceptable salts thereof, wherein $R^1$ is —$CF_3$, $R^2$ is —$CF_3$, $R^3$ is H, and ring A is selected from

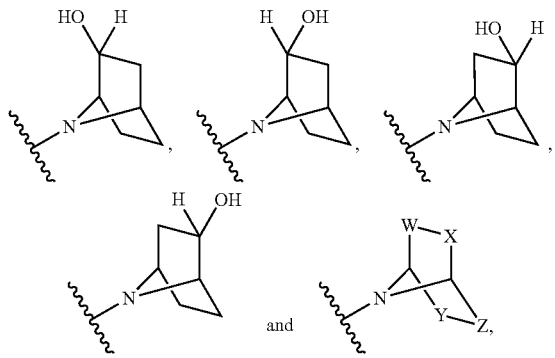

wherein two of W, X, Y and Z are —CH—OH and the other two are —$CH_2$—.

The compounds of Formula I and pharmaceutically acceptable compositions containing those compounds are useful for treating or lessening the severity of a variety of diseases, disorders, or conditions associated with mutations in CFTR.

DETAILED DESCRIPTION OF THE INVENTION

Compounds and Definitions

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR, R117H CFTR, and G551D CFTR (see, e.g., http://www.genet.sickkids.on.ca/cftr/app, for CFTR mutations).

The term "modulating" as used herein means increasing or decreasing by a measurable amount.

The term "normal CFTR" or "normal CFTR function" as used herein means wild-type like CFTR without any impairment due to environmental factors such as smoking, pollution, or anything that produces inflammation in the lungs.

The term "reduced CFTR" or "reduced CFTR function" as used herein means less than normal CFTR or less than normal CFTR function.

As used herein, the terms "ΔF508" and "F508del" are used interchangeably.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention; e.g., compounds of Formula I may exist as tautomers:

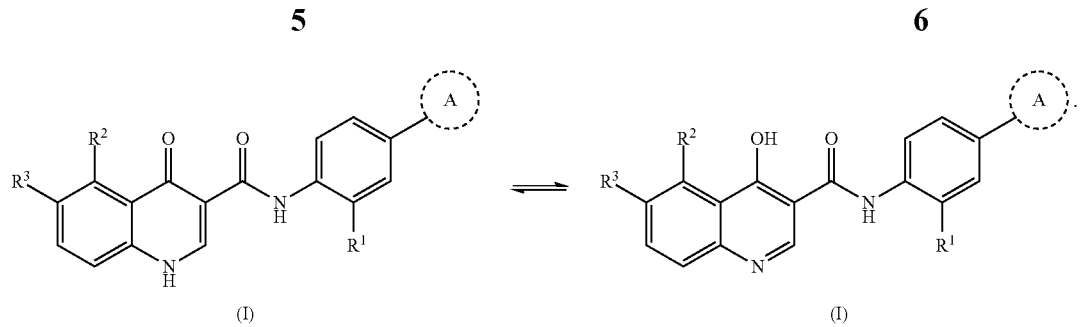

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays. Such compounds, particularly compounds that contain deuterium atoms, may exhibit modified metabolic properties.

Description of Exemplary Processes:

In one aspect, the invention includes compounds of Formula I:

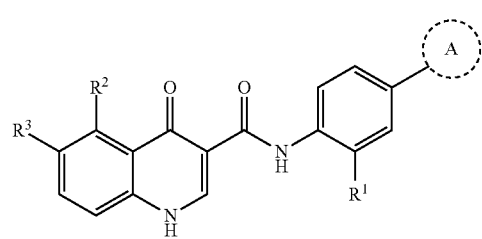

or pharmaceutically acceptable salts thereof, wherein $R^1$ is —$CF_3$, $R^2$ is —$CF_3$, $R^3$ is H, and ring A is selected from

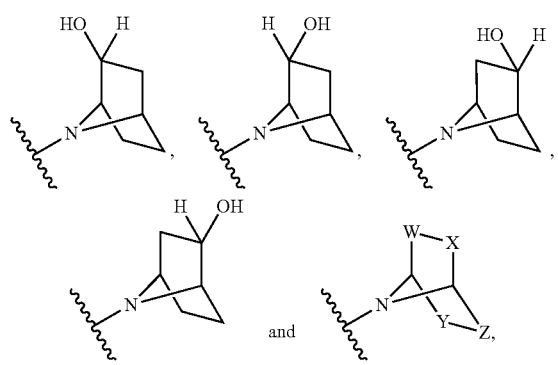

wherein two of W, X, Y and Z are —CH—OH and the other two are —$CH_2$—.

In another aspect, the invention includes a pharmaceutical composition comprising a compound of Formula I, or a salt thereof, and a pharmaceutically acceptable carrier or excipient.

In another aspect, the invention includes a pharmaceutical composition consisting essentially of a compound of Formula I, or a salt thereof, and a pharmaceutically acceptable carrier or excipient.

In another aspect, the invention relates to processes for producing the compounds of Formula I:

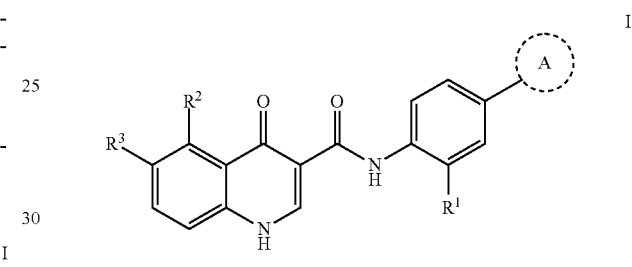

or pharmaceutically acceptable salts thereof, wherein $R^1$ is —$CF_3$, $R^2$ is —$CF_3$, $R^3$ is H, and ring A is selected from

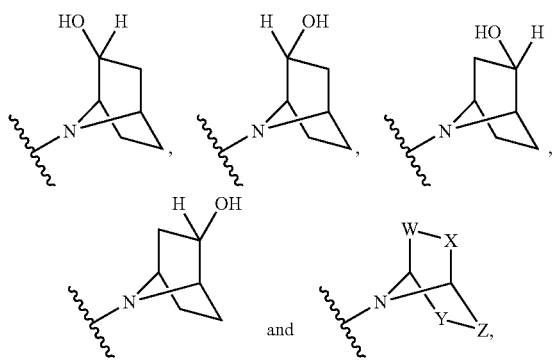

wherein two of W, X, Y and Z are —CH—OH and the other two are —$CH_2$—.

In one embodiment of this aspect, the invention includes processes for producing the compounds of Formula I, wherein ring A is selected from

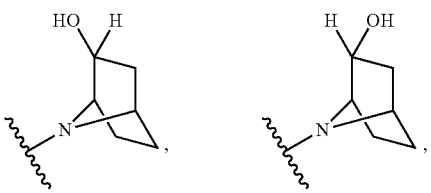

-continued

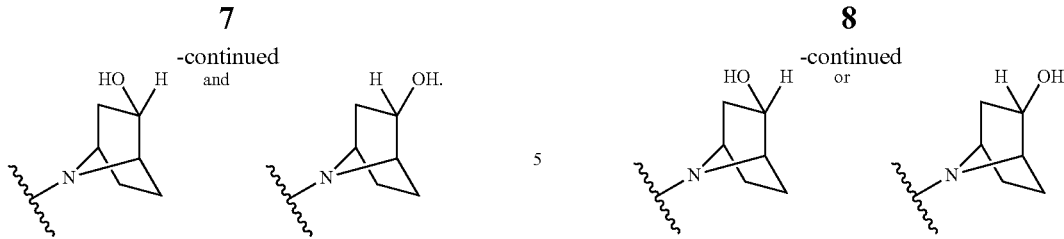

The process includes contacting the compound of Formula II with a CYP enzyme to produce a mixture of compounds of Formula I, wherein the compound of Formula II has the structure

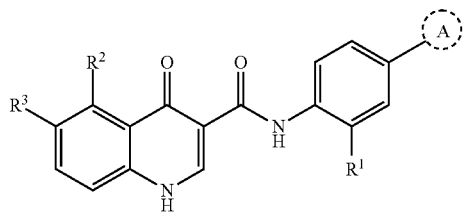

in which $R^1$ is —$CF_3$, $R^2$ is —$CF_3$, $R^3$ is H, and ring A is

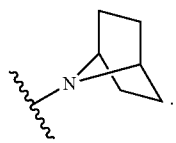 [SMILES: *N1C2CCC1CC2]

In one embodiment, the CYP enzyme is CYP-102.

In another embodiment, the CYP enzyme is CYP-102 from *Bacillus megaterium*.

In another embodiment, the CYP enzyme is CYP-102 from BM3-M11. See, for example, *J. Med. Chem.* 50:455-461 (2007).

In one embodiment, the process produces compounds of Formula I, wherein Ring A is

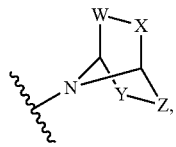

and W, X, Y and Z are defined as above, in a stepwise fashion by first producing compounds of Formula I, wherein Ring A is

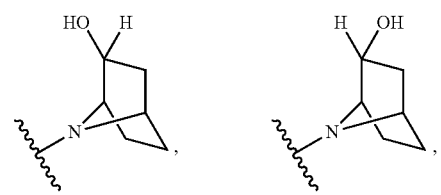

from a compound of Formula II.

In any of the foregoing embodiments, the process is optionally conducted in the presence of an organic solvent. For instance, the solvent is acetonitrile, methanol, acetone, dimethylsulfoxide, and dimethylformamide or mixtures thereof. In some specific embodiments, the process is conducted in the presence of methanol. In some instances the organic solvent is present in an amount of less than about 30% (v/v). In other instances, the organic solvent is present in an amount of less than about 25% (v/v). In other instances, the organic solvent is present in an amount of less than or equal to about 20% (v/v). In still other instances, the organic solvent is present in an amount of between about 5% to about 25% (v/v). In still other instances, the organic solvent is present in an amount of between about 10% to about 20% (v/v). In some embodiments in which the process includes an organic solvent, the yield of the compounds of Formula I is advantageously and unexpectedly improved relative to processes that lack the organic solvent.

In one aspect, the process produces a compound of Formula I, wherein Ring A is

and W, X, Y and Z are defined as above. In some embodiments of this aspect, the process results in a reduced yield of the product. In some further embodiments of this aspect, the process includes an organic solvent. In other embodiments, the yield is less than 10%. In some embodiments, the yield is less than 5%. In other embodiments, the yield is less than 2%. In some further embodiments, the yield is less than 1%. In still some further embodiments, the yield is less than 0.1%. In other embodiments, the most dramatic decrease in yield results when the organic solvent is present in an amount from about 10% to about 30%. In some further embodiments, the most dramatic decrease in yield results when the organic solvent is present in an amount from of about 20%. In some embodiments, the most dramatic decrease in yield is shown when the organic solvent is acetonitrile, methanol, acetone, dimethylsulfoxide, or dimethylformamide or mixtures thereof.

In one aspect of the process, the yield of the mixture of compounds of Formula I, wherein Ring A is

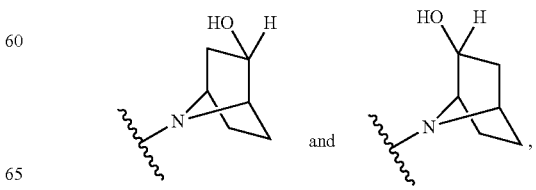

is greater relative to the mixture of compounds wherein Ring A is

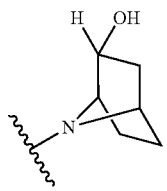 and 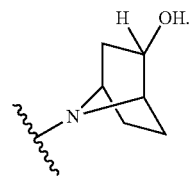

In one embodiment of this aspect, the process includes an organic solvent. In another embodiment, the organic solvent is acetonitrile. In another embodiment, the maximum yield is produced when acetonitrile is present in an amount from about 5% to about 15%. In a further embodiment, the maximum yield is produced when acetonitrile is present in an amount of about 10%.

In another embodiment of this aspect, the organic solvent is methanol. In one embodiment, the maximum yield is produced when methanol is present in an amount from about 10% to about 30%. In a further embodiment, the maximum yield is produced when methanol is present in an amount of about 20%. In one embodiment, the maximum yield relative to processes that lack the organic solvent is about 2 fold to 4 fold. In one further embodiment, the maximum yield relative to processes that lack the organic solvent is about 3 fold.

In another embodiment of this aspect, the organic solvent is DMSO. In one embodiment, the maximum yield is produced when DMSO is present in an amount from about 10% to about 30%. In a further embodiment, the maximum yield is produced when DMSO is present in an amount of about 20%.

In any of the foregoing embodiments, the process further comprises separating the mixture of compounds of Formula I. For instance, the exo and endo isomers and each of their enantiomeric pairs can be separated by chiral LC-MS/MS.

In one aspect, ring A of the separated isomer of Formula I is

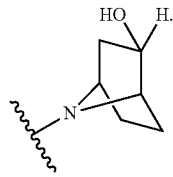

In yet another aspect, ring A of the separated isomer of Formula I is

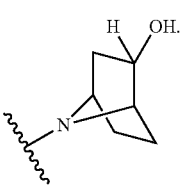 [SMILES: *N1C2CCC1C(O)C2]

In yet another aspect, ring A of the separated isomer of Formula I is

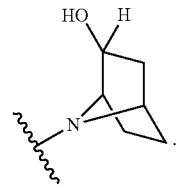

In still another aspect, ring A of the separated isomer of Formula I is

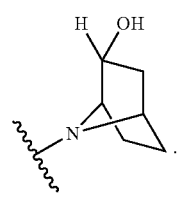 [SMILES: *N1C2CCC1C(O)C2]

In one embodiment, the compound of Formula I is selected from

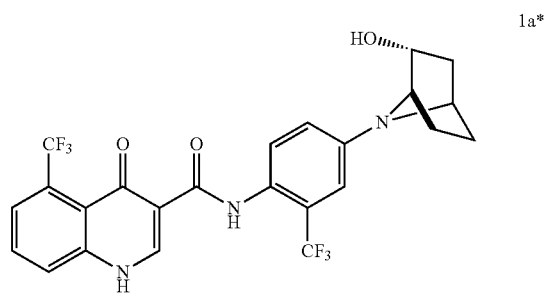

1a*

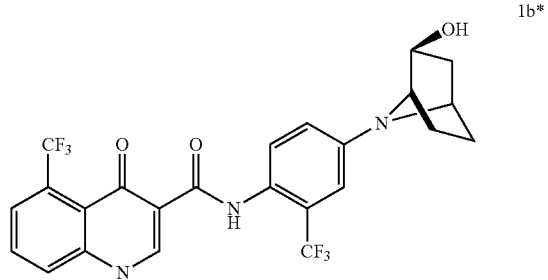

1b*

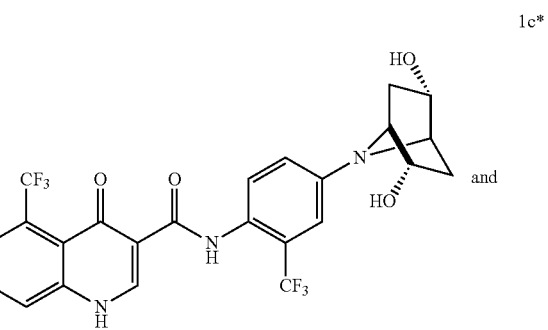

1c* and

-continued

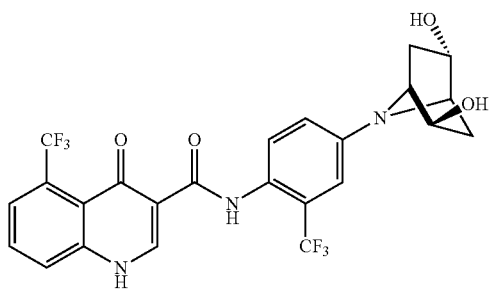

1d*

*Note:
Compounds 1a-1d are each drawn as a single enantiomer, but are meant to include all possible stereoisomers.

In one aspect, the invention relates to compounds of Formula III:

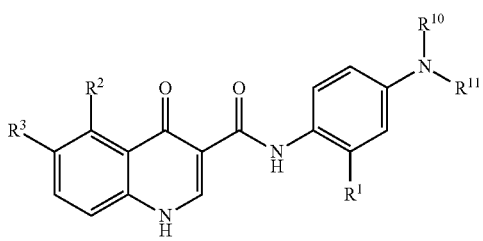

Formula III or pharmaceutically acceptable salt thereof, wherein $R^1$ is —$CF_3$, $R^2$ is —$CF_3$, $R^3$ is H, and $R^{10}$ and $R^{11}$ are each independently hydrogen; or $R^{10}$ and $R^{11}$ together with the nitrogen to which they are attached form a pyrrolidine or piperidine ring, each of which is optionally and independently substituted with up to 2 of —COOH, —$CH_2$COOH, —OH or —$CH_2$OH; or one of $R^{10}$ and $R^{11}$ is hydrogen, and the other of and $R^{10}$ and $R^{11}$ is a cyclopentane or cyclohexane ring, each of which is optionally and independently substituted with up to 2 of —COOH, —$CH_2$COOH, —OH or —$CH_2$OH.

In another aspect, the invention includes a pharmaceutical composition comprising a compound of Formula III, or a salt thereof, and a pharmaceutically acceptable carrier or excipient.

In another aspect, the invention includes a pharmaceutical composition consisting essentially of a compound of Formula III, or a salt thereof, and a pharmaceutically acceptable carrier or excipient.

In one aspect, the invention relates to processes for producing one or more of a compound of Formula III:

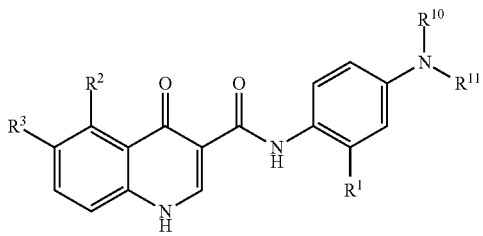

Formula III or pharmaceutically acceptable salt thereof, wherein $R^1$ is —$CF_3$, $R^2$ is —$CF_3$, $R^3$ is H, and $R^{10}$ and $R^{11}$ are each independently hydrogen; or $R^{10}$ and $R^{11}$ together with the nitrogen to which they are attached form a pyrrolidine or piperidine ring, each of which is optionally and independently substituted with up to 2 of —COOH, —$CH_2$COOH, —OH or —$CH_2$OH; or one of $R^{10}$ and $R^{11}$ is hydrogen, and the other of and $R^{10}$ and $R^{11}$ is a cyclopentane or cyclohexane ring, each of which is optionally and independently substituted with up to 2 of —COOH, —$CH_2$COOH, —OH or —$CH_2$OH.

In one embodiment of this aspect, the compound of Formula III is produced from a compound of Formula II.

In one embodiment of this aspect, the CYP enzyme is CYP-102.

In another embodiment, the CYP enzyme is CYP-102 from *Bacillus megaterium*.

In another embodiment, the CYP enzyme is CYP-102 from BM3-M11. See, for example, *J. Med. Chem.* 50:455-461 (2007).

In one embodiment, the process produces compounds of Formula III in a stepwise fashion by first producing compounds of Formula I, wherein Ring A is

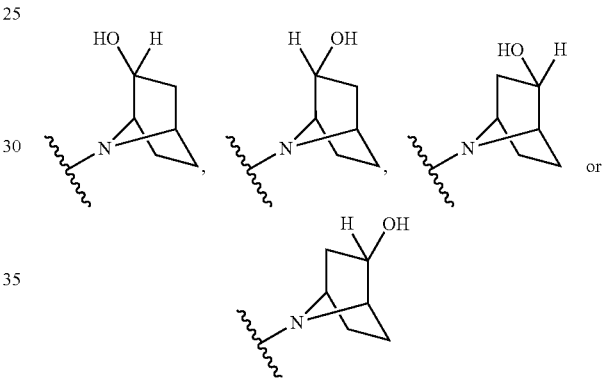

from a compound of Formula II.

In any of the foregoing embodiments, the process is optionally conducted in the presence of an organic solvent. For instance, the solvent is acetonitrile, methanol, acetone, dimethylsulfoxide, and dimethylformamide or mixtures thereof. In some specific embodiments, the process is conducted in the presence of methanol. In some instances the organic solvent is present in an amount of less than about 30% (v/v). In other instances, the organic solvent is present in an amount of less than about 25% (v/v). In other instances, the organic solvent is present in an amount of less than or equal to about 20% (v/v). In still other instances, the organic solvent is present in an amount of between about 5% to about 25% (v/v). In still other instances, the organic solvent is present in an amount of between about 10% to about 20% (v/v). In some embodiments in which the process includes an organic solvent, the yield of the compounds of Formula III is advantageously and unexpectedly improved relative to processes that lack the organic solvent.

In one aspect, the process produces a compound of Formula III. In some embodiments of this aspect, the process results in a reduced yield of the product. In some further embodiments of this aspect, the process includes an organic solvent. In other embodiments, the yield is less than 10%. In some embodiments, the yield is less than 5%. In other embodiments, the yield is less than 2%. In some further embodiments, the yield is less than 1%. In still some further embodiments, the yield is less than 0.1%. In other embodiments, the most dramatic decrease in yield results when the organic solvent is present in an amount from about 10% to about 30%. In some further embodiments, the most dramatic decrease in yield results when the organic solvent is present in an amount from of about 20%. In some embodiments, the most dramatic decrease in yield is shown when the organic solvent is acetonitrile, methanol, acetone, dimethylsulfoxide, or dimethylformamide or mixtures thereof.

In another embodiment of this aspect, the organic solvent is methanol. In one embodiment, the maximum yield is produced when methanol is present in an amount from about 10% to about 30%. In a further embodiment, the maximum yield is produced when methanol is present in an amount of about 20%. In one embodiment, the maximum yield relative to processes that lack the organic solvent is about 2 fold to 4 fold. In one further embodiment, the maximum yield relative to processes that lack the organic solvent is about 3 fold.

In another embodiment of this aspect, the organic solvent is DMSO. In one embodiment, the maximum yield is produced when DMSO is present in an amount from about 10% to about 30%. In a further embodiment, the maximum yield is produced when DMSO is present in an amount of about 20%.

In some embodiments of this aspect, the compound of Formula III is selected from:

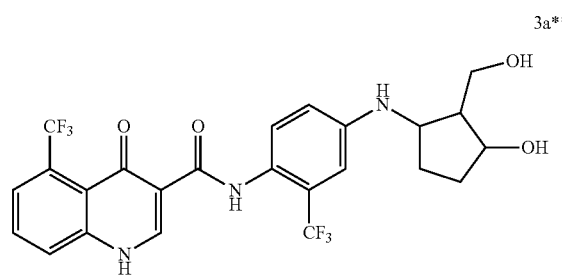

3a**

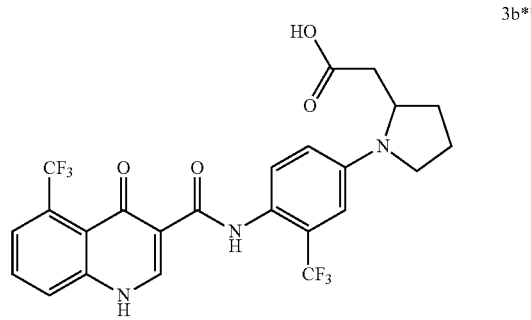

3b**

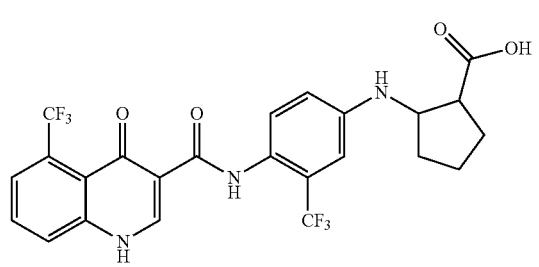

3c**

-continued

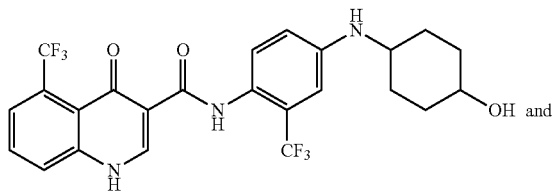

3d** and

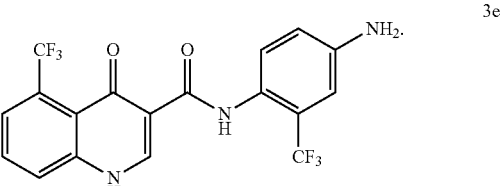

3e

**Further Note: Compounds 3a-3d are each drawn with non-specific stereochemistry and are meant to include all possible stereoisomers.

As described herein, the compounds of Formula III are meant to include all enantiomerically enriched and/or enantiomerically pure compounds of Formula III. In some embodiments, the invention includes a compound selected from 1a-1d and 3a-3e which is a single enantiomer, or a partially racemic mixture with an enrichment of a single enantiomer.

Uses, Formulation and Administration

Pharmaceutically Acceptable Compositions

In one aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, edisylate (ethanedisulfonate), ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating or lessening the severity of a condition, disease, or disorder implicated by CFTR mutation. In certain embodiments, the present invention provides a method of treating a condition, disease, or disorder implicated by a deficiency of the CFTR activity, the method comprising administering a composition comprising a compound of Formula I to a subject, preferably a mammal, in need thereof.

In another aspect, the invention also provides a method of treating or lessening the severity of a disease in a patient comprising administering to said patient one of the compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian, and myotonic dystrophy, as well as spongiform encephalopathies, such as hereditary Creutzfeldt-Jakob disease (due to prion protein processing defect), Fabry disease, Gerstmann-Sträussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In some embodiments, the method includes treating or lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes treating or lessening the severity of cystic fibrosis in a patient possessing the ΔF508 mutation of human CFTR comprising administering to said patient one of the compositions as defined herein. In one embodiment, the method includes treating or lessening the severity of cystic fibrosis in a patient possessing the G551D mutation of human CFTR comprising administering to said patient one of the compositions as defined herein. In one embodiment, the method includes treating or lessening the severity of cystic fibrosis in a patient possessing the ΔF508 mutation of human CFTR on at least one allele comprising administering to said patient one of the compositions as defined herein. In one embodiment, the method includes treating or lessening the severity of cystic fibrosis in a patient possessing the ΔF508 mutation of human CFTR on both alleles comprising administering to said patient one of the compositions as defined herein. In one embodiment, the method includes treating or lessening the severity of cystic fibrosis in a patient possessing the G551D mutation of human CFTR on at least one allele comprising administering to said patient one of the compositions as defined herein. In one embodiment, the method includes treating or lessening the severity of cystic fibrosis in a patient possessing the G551D mutation of human CFTR on both alleles comprising administering to said patient one of the compositions as defined herein.

In some embodiments, the method includes lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes lessening the severity of cystic fibrosis in a patient possessing the ΔF508 mutation of human CFTR comprising administering to said patient one of the compositions as defined herein. In one embodiment, the method includes lessening the severity of cystic fibrosis in a patient possessing the G551D mutation of human CFTR comprising administering to said patient one of the compositions as defined herein. In one embodiment, the method includes lessening the severity of cystic fibrosis in a patient possessing the ΔF508 mutation of human CFTR on at least one allele comprising administering to said patient one of the compositions as defined herein. In one embodiment, the method includes lessening the severity of cystic fibrosis in a patient possessing the ΔF508 mutation of human CFTR on both alleles comprising administering to said patient one of the compositions as defined herein. In one embodiment, the method includes lessening the severity of cystic fibrosis in a patient possessing the G551D mutation of human CFTR on at least one allele comprising administering to said patient one of the compositions as defined herein. In one embodiment, the method includes lessening the severity of cystic fibrosis in a patient possessing the G551D mutation of human CFTR on both alleles comprising administering to said patient one of the compositions as defined herein.

In some aspects, the invention provides a method of treating or lessening the severity of Osteoporosis in a patient comprising administering to said patient a compound of Formula I or a pharmaceutically acceptable salt thereof.

In certain embodiments, the method of treating or lessening the severity of Osteoporosis in a patient comprises administering to said patient a pharmaceutical composition as described herein.

In some aspects, the invention provides a method of treating or lessening the severity of Osteopenia in a patient comprising administering to said patient a compound of Formula I or a pharmaceutically acceptable salt thereof.

In certain embodiments, the method of treating or lessening the severity of Osteopenia in a patient comprises administering to said patient a pharmaceutical composition as described herein.

In some aspects, the invention provides a method of bone healing and/or bone repair in a patient comprising administering to said patient a compound of Formula I or a pharmaceutically acceptable salt thereof.

In certain embodiments, the method of bone healing and/or bone repair in a patient comprises administering to said patient a pharmaceutical composition as described herein.

In some aspects, the invention provides a method of reducing bone resorption in a patient comprising administering to said patient a compound of Formula I or a pharmaceutically acceptable salt thereof.

In certain embodiments, the method of reducing bone resorption in a patient comprises administering to said patient a pharmaceutical composition as described herein.

In some aspects, the invention provides a method of increasing bone deposition in a patient comprising administering to said patient a compound of Formula I or a pharmaceutically acceptable salt thereof.

In certain embodiments, the method of increasing bone deposition in a patient comprises administering to said patient a pharmaceutical composition as described herein.

In some aspects, the invention provides a method of treating or lessening the severity of COPD in a patient comprising administering to said patient a compound of Formula I or a pharmaceutically acceptable salt thereof.

In certain embodiments, the method of treating or lessening the severity of COPD in a patient comprises administering to said patient a pharmaceutical composition as described herein.

In some aspects, the invention provides a method of treating or lessening the severity of smoke induced COPD in a patient comprising administering to said patient a compound of Formula I or a pharmaceutically acceptable salt thereof.

In certain embodiments, the method of treating or lessening the severity of smoke induced COPD in a patient comprises administering to said patient a pharmaceutical composition as described herein.

In some aspects, the invention provides a method of treating or lessening the severity of chronic bronchitis in a patient comprising administering to said patient a compound of Formula I or a pharmaceutically acceptable salt thereof.

In certain embodiments, the method of treating or lessening the severity of chronic bronchitis in a patient comprises administering to said patient a pharmaceutical composition as described herein.

In certain embodiments, the present invention provides a method of treating diseases associated with reduced CFTR function due to mutations in the gene encoding CFTR or environmental factors (e.g., smoke). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma.

In certain embodiments, the present invention provides a method for treating diseases associated with normal CFTR function. These diseases include, chronic obstructive pulmonary disease (COPD), chronic bronchitis, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, hereditary emphysema, gallstones, gastroesophageal reflux disease, gastrointestinal malignancies, inflammatory bowel disease, constipation, diabetes, arthritis, osteoporosis, and osteopenia.

In certain embodiments, the present invention provides a method for treating diseases associated with normal CFTR function including hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Pelizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebellar ataxia type I, spinal and bulbar muscular atrophy, dentatorubral pallidoluysian, and myotonic dystrophy, as well as spongiform encephalopathies, such as hereditary Creutzfeldt-Jakob disease (due to prion protein processing defect), Fabry disease, Gerstmann-Sträussler-Scheinker syndrome, Gorham's Syndrome, chloride channelopathies, myotonia congenita (Thomson and Becker forms), Bartter's syndrome type III, Dent's disease, hyperekplexia, epilepsy, lysosomal storage diseases, Angelman syndrome, Primary Ciliary Dyskinesia (PCD), PCD with situs inversus (also known as Kartagener syndrome), PCD without situs inversus and ciliary aplasia, or Sjogren's disease, comprising the step of administering to said mammal an effective amount of a composition comprising a compound of the present invention.

According to an alternative preferred embodiment, the present invention provides a method of treating cystic fibrosis comprising the step of administering to said mammal a composition comprising the step of administering to said mammal an effective amount of a composition comprising a compound of the present invention.

According to the invention an "effective amount" of the compound or pharmaceutically acceptable composition is that amount effective for treating or lessening the severity of one or more of the diseases, disorders or conditions as recited above.

The compounds and compositions, according to the method of the present invention, may be administered using any amount and any route of administration effective for treating or lessening the severity of one or more of the diseases, disorders or conditions as recited above.

In certain embodiments, the compounds and compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, the compounds and compositions of the present invention are useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, the compounds and compositions of the present invention are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Transmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, the compounds and compositions of the present invention are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The activity of a compound utilized in this invention as a modulator of CFTR may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, a bronchodialator, an anti-biotic, an anti-infective agent, an anti-inflammatory agent, a CFTR modulator other than a compound of the present invention, or a nutritional agent. In a further embodiment, the additional agent is a CFTR modulator other than a compound of the present invention.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodilators include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexaenoic acid (DHA), sildenafil, inhaled glutathione, pioglitazone, hydroxychloroquine, or simavastatin.

In another embodiment, the additional agent reduces the activity of the epithelial sodium channel blocker (ENaC) either directly by blocking the channel or indirectly by modulation of proteases that lead to an increase in ENaC activity (e.g., seine proteases, channel-activating proteases). Exemplary such agents include camostat (a trypsin-like protease inhibitor), QAU145, 552-02, GS-9411, INO-4995, Aerolytic, and amiloride. Additional agents that reduce the activity of the epithelial sodium channel blocker (ENaC) can be found, for example in PCT Publication No. WO2009/074575, the entire contents of which are incorporated herein in their entirety.

Amongst other diseases described herein, combinations of CFTR modulators, such as compounds of Formula I, and agents that reduce the activity of ENaC are use for treating Liddle's syndrome, an inflammatory or allergic condition including cystic fibrosis, primary ciliary dyskinesia, chronic bronchitis, chronic obstructive pulmonary disease, asthma, respiratory tract infections, lung carcinoma, xerostomia and keratoconjunctivitis sire, respiratory tract infections (acute and chronic; viral and bacterial) and lung carcinoma.

Combinations of CFTR modulators, such as compounds of Formula I, and agents that reduce the activity of ENaC are also useful for treating diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics (For convenience this particular asthmatic condition is referred to as "wheezy-infant syndrome"). Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. In some embodiments, the combinations of CFTR modulators, such as compounds of Formula I, and agents that reduce the activity of ENaC are useful for the treatment of bronchitis of whatever type or genesis including, e.g., acute, arachidic, catarrhal, croupous, chronic or phthinoid bronchitis.

In another embodiment, the additional agent is a CFTR modulator other than a compound of Formula I, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl) cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with a compound of Formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with a compound of Formula I. In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with a compound of Formula I.

According to another preferred embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells." *Biophys J* 69(4): 1272-80, and Gonzalez, J. E. and R. Y. Tsien (1997); "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of CFTR or a fragment thereof in a biological sample in vitro or in vivo comprising (i) a composition comprising a compound of Formula I or any of the above embodiments; and (ii) instructions for a) contacting the composition with the biological sample and b) measuring activity of said CFTR or a fragment thereof. In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of a composition of Formula I. In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

Intermediate 1

4-Oxo-5-(trifluoromethyl)-1,4-dihydroquinoline-3-carboxylic acid (17)

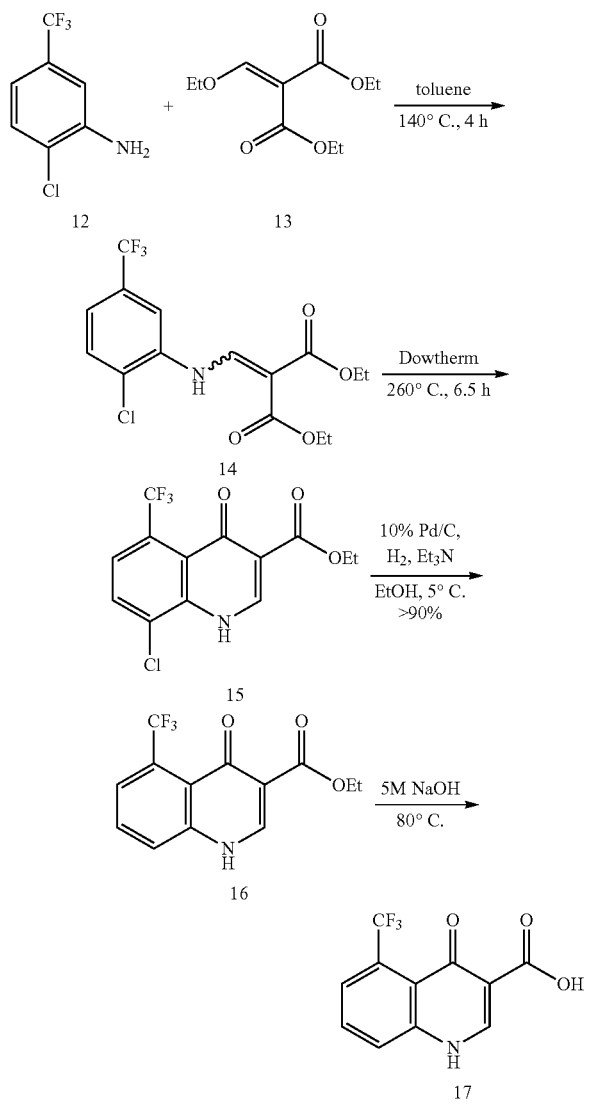

Example 1a

Diethyl 2-((2-chloro-5-(trifluoromethyl)phenylamino)methylene)malonate (14)

2-Chloro-5-(trifluoromethyl)aniline 12 (200 g, 1.023 mol), diethyl 2-(ethoxymethylene)malonate 13 (276 g, 1.3 mol) and toluene (100 mL) were combined under a nitrogen atmosphere in a three-neck, 1-L round bottom flask equipped with Dean-Stark condenser. The solution was heated with stirring to 140° C. and the temperature was maintained for 4 h. The reaction mixture was cooled to 70° C. and hexane (600 mL) was slowly added. The resulting slurry was stirred and allowed to warm to room temperature. The solid was collected by filtration, washed with 10% ethyl acetate in hexane (2×400 mL) and then dried under vacuum to provide a white solid (350 g, 94% yield) as the desired condensation product diethyl 2-((2-chloro-5-(trifluoromethyl)phenylamino)methylene)malonate 14. $^1$H NMR (400 MHz, DMSO-$d_6$) δ 11.28 (d, J=13.0 Hz, 1H), 8.63 (d, J=13.0 Hz, 1H), 8.10 (s, 1H), 7.80 (d, J=8.3 Hz, 1H), 7.50 (dd, J=1.5, 8.4 Hz, 1H), 4.24 (q, J=7.1 Hz, 2H), 4.17 (q, J=7.1 Hz, 2H), 1.27 (m, 6H).

Example 1b

Ethyl 8-chloro-4-oxo-5-(trifluoromethyl)-1,4-dihydroquinoline-3-carboxylate (15)

Method 1

A 3-neck, 1-L flask was charged with Dowtherm® (200 mL, 8 mL/g), which was degassed at 200° C. for 1 h. The solvent was heated to 260° C. and charged in portions over 10 min with diethyl 2-((2-chloro-5-(trifluoromethyl)phenylamino)methylene)malonate 14 (25 g, 0.07 mol). The resulting mixture was stirred at 260° C. for 6.5 hours (h) and the resulting ethanol byproduct removed by distillation. The mixture was allowed to slowly cool to 80° C. Hexane (150 mL) was slowly added over 30 minutes (min), followed by an additional 200 mL of hexane added in one portion. The slurry was stirred until it had reached room temperature. The solid was filtered, washed with hexane (3×150 mL), and then dried under vacuum to provide ethyl 8-chloro-4-oxo-5-(trifluoromethyl)-1,4-dihydroquinoline-3-carboxylate 15 as a tan solid (13.9 g, 65% yield). $^1$H NMR (400 MHz, DMSO-$d_6$) δ 11.91 (s, 1H), 8.39 (s, 1H), 8.06 (d, J=8.3 Hz, 1H), 7.81 (d, J=8.4 Hz, 1H), 4.24 (q, J=7.1 Hz, 2H), 1.29 (t, J=7.1 Hz, 3H).

Method 2

Compound 14 (2000 g, 5.468 mol) was introduced into the reactor. Dowtherm (4.000 L) was charged to the reactor and degassed at room temperature overnight with nitrogen purge. It was then stirred and warmed to 260° C. EtOH produced was distilled off. The reaction was monitored and was complete after 5.5 h. The heat source was removed and the reaction mixture was cooled to 80° C. and heptane (2.000 L) was charged. The mixture was stirred for 30 min. Heptane (6.000 L) was charged to the stirred mixture and stirring continued overnight. Solids were filtered off and washed with heptane (4.000 L) and dried in a vacuum oven at 50° C. to provide Compound 15.

Example 1c

Ethyl 4-oxo-5-(trifluoromethyl)-1H-quinoline-3-carboxylate (16)

A 3-neck, 5-L flask was charged with of ethyl 8-chloro-4-oxo-5-(trifluoromethyl)-1,4-dihydroquinoline-3-carboxylate 15 (100 g, 0.3 mol), ethanol (1250 mL, 12.5 mL/g) and triethylamine (220 mL, 1.6 mol). The vessel was then charged with 10 g of 10% Pd/C (50% wet) at 5° C. The reaction was stirred vigorously under hydrogen atmosphere for 20 h at 5° C., after which time the reaction mixture was concentrated to a volume of approximately 150 mL. The product, ethyl 4-oxo-5-(trifluoromethyl)-1H-quinoline-3-carboxylate 16, as a slurry with Pd/C, was taken directly into the next step.

Example 1d

4-Oxo-5-(trifluoromethyl)-1,4-dihydroquinoline-3-carboxylic acid (17)

Ethyl 4-oxo-5-(trifluoromethyl)-1H-quinoline-3-carboxylate 16 (58 g, 0.2 mol, crude reaction slurry containing Pd/C) was suspended in NaOH (814 mL of 5 M, 4.1 mol) in a 1-L flask with a reflux condenser and heated at 80° C. for 18 h, followed by further heating at 100° C. for 5 h. The reaction was filtered warm through packed Celite to remove Pd/C and the Celite was rinsed with 1 N NaOH. The filtrate was acidified to about pH 1 to obtain a thick, white precipitate. The precipitate was filtered then rinsed with water and cold acetonitrile. The solid was then dried under vacuum to provide 4-oxo-5-(trifluoromethyl)-1,4-dihydroquinoline-3-carboxylic acid 17 as a white solid (48 g, 92% yield). $^1$H NMR (400.0 MHz, DMSO-$d_6$) δ 15.26 (s, 1H), 13.66 (s, 1H), 8.98 (s, 1H), 8.13 (dd, J=1.6, 7.8 Hz, 1H), 8.06-7.99 (m, 2H).

Alternative Preparation of Intermediate 1

4-Oxo-5-(trifluoromethyl)-1,4-dihydroquinoline-3-carboxylic acid (17)

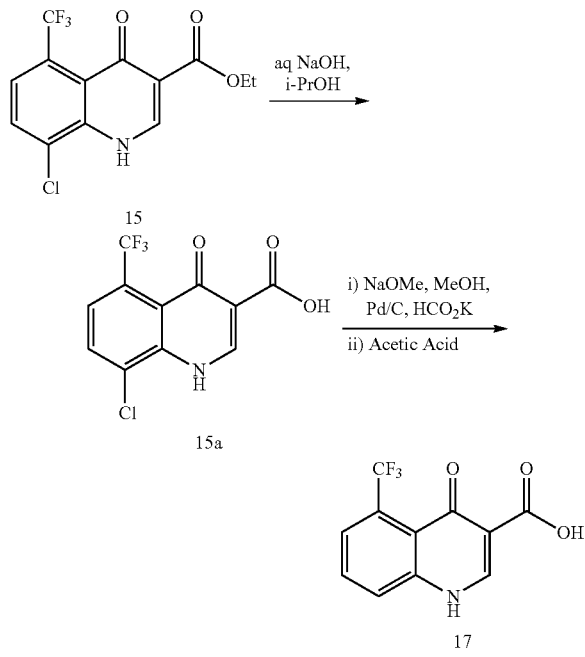

Example 1e 8-chloro-4-oxo-5-(trifluoromethyl)-1,4-dihydroquinoline-3-carboxylic acid (15a)

Ethyl 8-chloro-4-oxo-5-(trifluoromethyl)-1,4-dihydroquinoline-3-carboxylate (15) (1200 g, 3.754 mol) was charged into a reaction vessel followed by the addition of 2-propanol (1.200 L) and water (7.200 L) and stirred. Sodium hydroxide (600.6 g, 7.508 mol) and water (1.200 L) were mixed and allowed to cool to room temperature. The resulting mixture was charged into the reaction vessel and then was heated to 80° C. and stirred for 3.5 h to generate a dark, homogenous mixture. After an additional hour, acetic acid (9.599 L of 20% w/v, 31.97 mol) was added via dropping funnel over 45 min. The reaction mixture was cooled with stirring to 22° C. at a rate of 6° C./h. The resulting solid was filtered and washed with water (3 L) to generate a wet cake (1436 g). The filtrate was dried in a vacuum oven with a nitrogen bleed over Drierite® to generate 8-chloro-4-oxo-5-(trifluoromethyl)-1,4-dihydroquinoline-3-carboxylic acid as a brown solid (1069 g). The 8-chloro-4-oxo-5-(trifluoromethyl)-1,4-dihydroquinoline-3-carboxylic acid was purified by slurrying in 1.5 L methanol and stirring for 6 h. It was then filtered and dried to furnish 968.8 g of purified 8-chloro-4-oxo-5-(trifluoromethyl)-1,4-dihydroquinoline-3-carboxylic acid.

Example 1f 4-oxo-5-(trifluoromethyl)-1,4-dihydroquinoline-3-carboxylic acid (17)

Compound 15a (18.5 g, 1.00 eq, limiting reagent) was charged into a reaction vessel and MeOH (118 mL, 6.4 vol) was added under inert atmosphere with agitation. Sodium methoxide (3.53 g, 1.00 eq.) was added portion wise over 10 min to the reactor. The mixture was stirred until all solids are in solution (5-10 minutes). Palladium on carbon (2.7 g, 0.03 eq) was then added to the reaction mixture. Potassium formate (10.78 g, 2 eq.) dissolved in MeOH (67 mL, 3.6 vol) was added to the reaction mixture over 30 min [Alternatively, the potassium formate reagent may be replaced with hydrogen gas]. It was then stirred for about 4.5 h at ambient temperature. The reaction was judged complete when 8-chloro-4-oxo-5-(trifluoromethyl)-1,4-dihydroquinoline-3-carboxylic acid was no more than 1.0% relative to 4-oxo-5-(trifluoromethyl)-1,4-dihydroquinoline-3-carboxylic acid (17). When the reaction was complete, the mixture was filtered through a pad of Celite (mass of Celite used approximately 2× mass of 8-chloro-4-oxo-5-(trifluoromethyl)-1,4-dihydroquinoline-3-carboxylic acid charged into the vessel at the start) to remove solids. The Celite cake was washed with MeOH (37 mL, 2 vol). The filtrate was charged into a clean reaction vessel and stirred. Acetic acid (7.22 mL, 2 eq.) was charged continuously to the stirred solution over at least 45 minutes and the resulting slurry stirred for between 5-16 h. The solid was filtered and the cake washed with MeOH (56 mL, 3 vol), suction-dried and then vacuum dried to give the title compound as an white/off white solid.

Intermediate 2

4-(7-Azabicyclo[2.2.1]heptan-7-yl)-2-(trifluoromethyl)aniline (20)

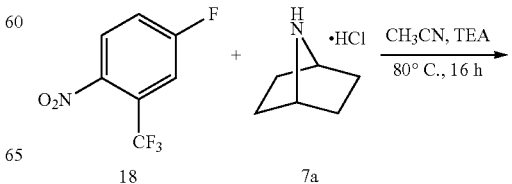

-continued

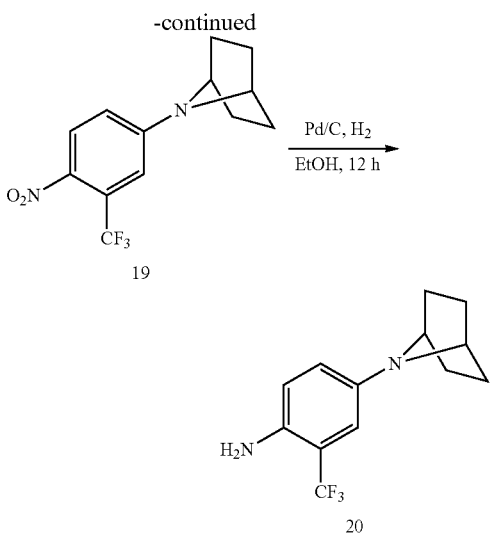

Example 1g

7-[4-Nitro-3-(trifluoromethyl)phenyl]-7-azabicyclo[2.2.1]heptane (19)

Method 1

To a flask containing 7-azabicyclo[2.2.1]heptane hydrochloride 7a (4.6 g, 34.43 mmol, obtained from Tyger Scientific Inc., 324 Stokes Avenue, Ewing, N.J., 08638 USA under a nitrogen atmosphere was added a solution of 4-fluoro-1-nitro-2-(trifluoromethyl)benzene 18 (6.0 g, 28.69 mmol) and triethylamine (8.7 g, 12.00 mL, 86.07 mmol) in acetonitrile (50 mL). The reaction flask was heated at 80° C. under a nitrogen atmosphere for 16 h. The reaction mixture was allowed to cool and then was partitioned between water and dichloromethane. The organic layer was washed with 1 M HCl, dried over $Na_2SO_4$, filtered, and concentrated to dryness. Purification by silica gel chromatography (0-10% ethyl acetate in hexanes) yielded 7-[4-nitro-3-(trifluoromethyl)phenyl]-7-azabicyclo[2.2.1]heptane (19) (7.2 g, 88% yield) as a yellow solid. $^1$H NMR (400.0 MHz, DMSO-$d_6$) δ 8.03 (d, J=9.1 Hz, 1H), 7.31 (d, J=2.4 Hz, 1H), 7.25 (dd, J=2.6, 9.1 Hz, 1H), 4.59 (s, 2H), 1.69-1.67 (m, 4H), 1.50 (d, J=7.0 Hz, 4H).

Method 2

4-Fluoro-1-nitro-2-(trifluoromethyl)benzene (18) (901 g, 4.309 mol) was introduced into a 30 L jacketed vessel along with $Na_2CO_3$ (959.1 g, 9.049 mol) and DMSO (5 L, 5.5 vol) under nitrogen atmosphere and stirring. 7-azabicyclo[2.2.1]heptane hydrochloride (7a) (633.4 g, 4.740 mol) was then added to the vessel in portions. The temperature was gradually raised to 55° C. When the reaction was substantially complete, the mixture was diluted with 10 vol EtOAc and washed with water (5.5 vol) three times or until DMSO in the aqueous layer disappeared (HPLC). The organic layer was concentrated to 4 vol and then the solvent was swapped with cyclohexane until all the EtOAc was removed, and the total volume in the flask was about 4 vol containing cyclohexane. The reaction mixture was heated to 60° C. on a rotary evaporator for 30 min. Then the solution was cooled to room temperature with stirring or rotation for 3 h. When all the solid crystallized, the solution was concentrated to dryness to provide 7-[4-nitro-3-(trifluoromethyl)phenyl]-7-azabicyclo[2.2.1]heptane (19).

Method 3

4-Fluoro-1-nitro-2-(trifluoromethyl)benzene (18) was dissolved in 3 vol DCM. Tetrabutylammoniumbromide (0.05 eq) and KOH (50 wt %, 3.6 eq) were added. 7-azabicyclo[2.2.1]heptane hydrochloride (7a) was then added at 0-5° C. The reaction was warmed up to ambient temperature and monitored by HPLC. Once substantially complete, the layers were separated and the organic layer was washed with 1M HCl. The layers were separated and the aqueous layer was discarded. The organic layer was washed once with water, once with brine, and then distilled. The resulting material was recrystallized from cyclohexane at reflux. The solid was filtered, washed with cyclohexane, and dried in a vacuum oven at 45° C. with a $N_2$ gas bleed to provide 7-[4-nitro-3-(trifluoromethyl)phenyl]-7-azabicyclo[2.2.1]heptane (19).

Example 1h

4-(7-Azabicyclo[2.2.1]heptan-7-yl)-2-(trifluoromethyl)aniline (20)

A flask charged with 7-[4-nitro-3-(trifluoromethyl)phenyl]-7-azabicyclo[2.2.1]heptane 19 (7.07 g, 24.70 mmol) and 10% Pd/C (0.71 g, 6.64 mmol) was evacuated and then flushed with nitrogen. Ethanol (22 mL) was added and the reaction flask was fitted with a hydrogen balloon. After stirring vigorously for 12 h, the reaction mixture was purged with nitrogen and Pd/C was removed by filtration. The filtrate was concentrated to a dark oil under reduced pressure and the residue purified by silica gel chromatography (0-15% ethyl acetate in hexanes) to provide 4-(7-azabicyclo[2.2.1]heptan-7-yl)-2-(trifluoromethyl)aniline (20) as a purple solid (5.76 g, 91% yield). $^1$H NMR (400.0 MHz, DMSO-$d_6$) δ 6.95 (dd, J=2.3, 8.8 Hz, 1H), 6.79 (d, J=2.6 Hz, 1H), 6.72 (d, J=8.8 Hz, 1H), 4.89 (s, 2H), 4.09 (s, 2H), 1.61-1.59 (m, 4H) and 1.35 (d, J=6.8 Hz, 4H).

Example 1i

Preparation of the hydrochloride salt of 4-(7-azabicyclo[2.2.1]heptan-7-yl)-2-(trifluoromethyl)aniline (20-HCl)

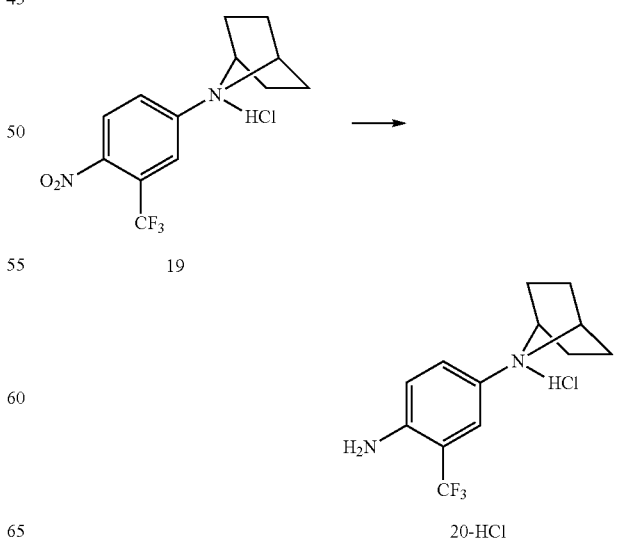

Palladium on carbon (150 g, 5% w/w) was charged into a Büchi Hydrogenator (20 L capacity) under a nitrogen atmosphere followed by the addition of the hydrochloride salt of 7-[4-nitro-3-(trifluoromethyl)phenyl]-7-azabicyclo[2.2.1]heptane (19) (1500 g) and 2-methyltetrahydrofuran (10.5 L, 7 vol). Hydrogen gas was charged into the closed vessel to a pressure of +0.5 bar above atmospheric pressure. A vacuum was applied for about 2 min followed by the introduction of hydrogen gas to a pressure of 0.5 bar. This process was repeated 2 times. Then hydrogen gas was continuously charged at +0.5 bar above atmospheric pressure. The mixture was stirred and the temperature was maintained between 18° C. and 23° C. by cooling the jacket of the vessel. Once the reaction consumed no more hydrogen and evolved no more heat, a vacuum was again applied. Nitrogen gas was charged into the vessel at 0.5 bar and a vacuum was reapplied followed by a second charge of 0.5 bar nitrogen gas. When the reaction was substantially complete, the reaction mixture was transferred into a receiving flask under nitrogen atmosphere via a filter funnel using a Celite filter. The Celite filter cake was washed with 2-methyltetrahydrofuran (3 L, 2 vol). The washings and filtrate were charged into a vessel equipped with stirring, temperature control, and a nitrogen atmosphere. 4M HCl in 1,4-dioxane (1 vol) was added continuously over 1 h into the vessel at 20° C. The mixture was stirred for an additional 10 h (or overnight), filtered, and washed with 2-methyltetrahydrofuran (2 vol) and dried to generate 1519 g of the of 4-(7-azabicyclo[2.2.1]heptan-7-yl)-2-(trifluoromethyl)aniline hydrochloride (20-HCl) as a white crystalline solid.

Example 1j

Preparation of the Compound of Formula II

To a solution of 4-oxo-5-(trifluoromethyl)-1H-quinoline-3-carboxylic acid 17 (9.1 g, 35.39 mmol) and 4-(7-azabicyclo[2.2.1]heptan-7-yl)-2-(trifluoromethyl)aniline 20 (9.2 g, 35.74 mmol) in 2-methyltetrahydrofuran (91.00 mL) was added propyl phosphonic acid cyclic anhydride (T3P, 50% solution in ethyl acetate, 52.68 mL, 88.48 mmol) and pyridine (5.6 g, 5.73 mL, 70.78 mmol) at room temperature. The reaction flask heated at 65° C. for 10 h under a nitrogen atmosphere. After cooling to room temperature, the reaction was then diluted with ethyl acetate and quenched with saturated $Na_2CO_3$ solution (50 mL). The layers were separated, and the aqueous layer was extracted twice more with ethyl acetate. The combined organic layers were washed with water, dried over $Na_2SO_4$, filtered and concentrated to a tan solid. The crude solid product was slurried in ethyl acetate/diethyl ether (2:1), collected by vacuum filtration, and washed twice more with ethyl acetate/diethyl ether (2:1) to provide the product as a light yellow crystalline powder. The powder was dissolved in warm ethyl acetate and absorbed onto Celite. Purification by silica gel chromatography (0-50% ethyl acetate in dichloromethane) provided N-(4-(7-azabicyclo[2.2.1]heptan-7-yl)-2-(trifluoromethyl)phenyl)-4-oxo-5-(trifluoromethyl)-1,4-dihydroquinoline-3-carboxamide as a white crystalline solid (13.5 g, 76% yield). LC/MS m/z 496.0 [M+H]$^+$, retention time 1.48 min (RP-$C_{18}$, 10-99% $CH_3CN$/0.05% TFA over 3 min). $^1$H NMR (400.0 MHz, DMSO-$d_6$) δ 13.08 (s, 1H), 12.16 (s, 1H), 8.88 (s, 1H), 8.04 (dd, J=2.1, 7.4 Hz, 1H), 7.95-7.88 (m, 3H), 7.22 (dd, 2.5, 8.9 Hz, 1H), 7.16 (d, J=2.5 Hz, 1H), 4.33 (s, 2H), 1.67 (d, J=6.9 Hz, 4H), 1.44 (d, J=6.9 Hz, 4H).

Synthesis of 7-azabicyclo[2.2.1]heptane hydrochloride (7a)

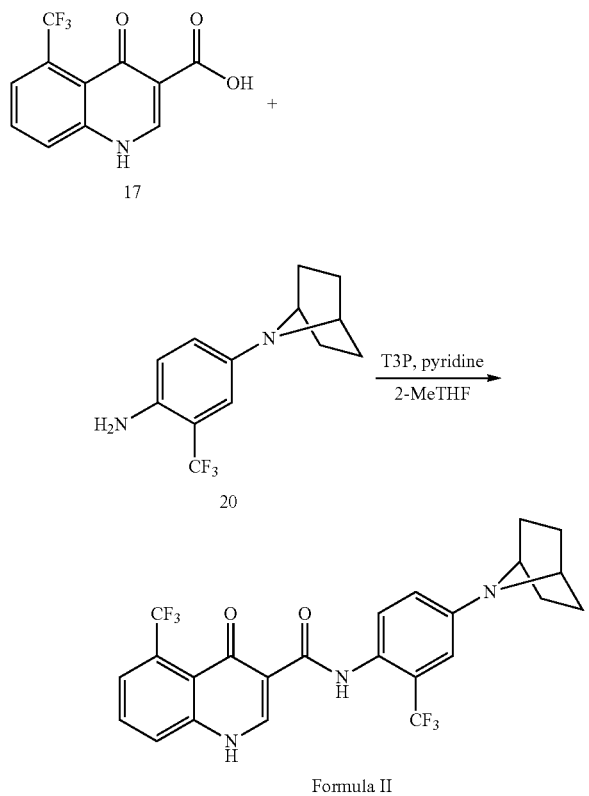

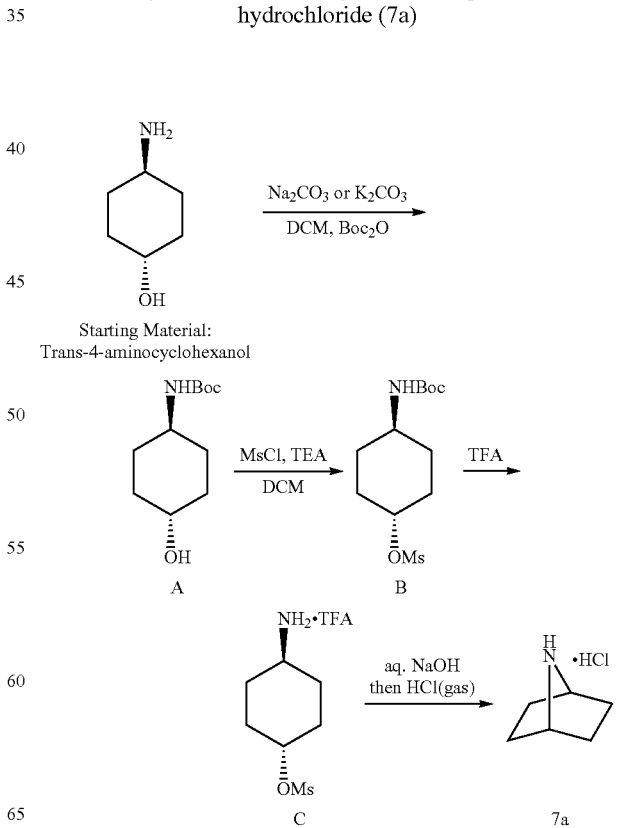

Example 1k

Preparation of trans-4-(tert-butoxycarbonylamino)cyclohexanol (A)

Method 1.

Sodium carbonate (920.2 g, 8.682 mol, 2 eq) was added to a reaction vessel followed by an addition of water (3.000 L, 6 vol) and stirring. Dichloromethane (DCM, 4.000 L, 4 vol) was added followed by trans-4-aminocyclohexanol (500.0 g, 4.341 mol) to generate a biphasic reaction mixture that was vigorously stirred at room temperature. A solution of $Boc_2O$ (947.4 g, 997.3 mL, 4.341 mol, 1 eq) in DCM (2 vol) was then rapidly added dropwise to the vessel, and the resulting reaction mixture was stirred at room temperature overnight. The reaction mixture was then filtered and the filter cake was washed with water (2×8 vol). The product was suction-dried until it was a compact cake. The cake was then dried in a vacuum oven at 35° C. for 24 h giving 830 g of trans-4-(tert-butoxycarbonylamino)cyclohexanol (A) as a crystalline solid.

Method 2.

Two 50 L three-neck round bottom flasks were each equipped with a mechanical stirrer and thermocouple. The flasks were placed in a cooling tub, and then each flask was charged with water (8.87 L) and trans-4-aminocyclohexanol (1479 g). After about 10 to 30 minutes, the trans-4-aminocyclohexanol had dissolved, and potassium carbonate (1774.6 g) was added to each flask. After about 10 to 20 minutes, the potassium carbonate had dissolved, and DCM (2.96 L) was charged to each flask. Boc anhydride (3082.6 g) in DCM (1479 mL) was then added to each flask at such a rate as to maintain the temperature at 20 to 30° C. An ice/water bath was used to control the exotherm and to accelerate the addition, which took approximately 1 to 2 hours. A suspension formed during the addition, and the reaction mixtures were allowed to warm to room temperature and stirred overnight, until the reaction was complete based on the disappearance of the Boc anhydride. Heptane (6 L) was then charged to each flask, and the mixtures were cooled to approximately 0 to 5° C. Solids were collected from each flask by filtration using the same filter. The combined solids were washed with heptane (6 L) followed by water (8 L). The solids were charged to an appropriately sized crock equipped with a mechanical stirrer. Water (12 L) and heptane (6 L) were added, and the resulting suspension was mechanically stirred for 30 to 60 minutes. The solids were collected by filtration and then washed on a filter with water (8 L) and heptane (8 L), air-dried on a filter for three days, and then dried under vacuum at 30 to 35° C. to a constant weight to provide the product as a white solid.

Example 1l

Preparation of trans-4-(tert-butoxycarbonylamino) cyclohexylmethanesulfonate (B)

Method 1.

A 12 L flask was equipped with a nitrogen flow and a mechanical stirrer. Trans-4-(tert-butoxycarbonylamino)cyclohexanol (750 g, 3.484 mol) was introduced, followed by tetrahydrofuran (THF, 6.000 L, 8 vol), and the mixture was stirred. Triethylamine (370.2 g, 509.9 mL, 3.658 mol, 1.05 eq) was added and the mixture was cooled to 0° C. Methanesulfonyl chloride (419.0 g, 283.1 mL, 3.658 mol, 1.05 eq) was carefully added dropwise, keeping the temperature of the mixture below 5° C. After the addition, the mixture was stirred at 0° C. for 3 h, and then gradually warmed to room temperature (17° C.) and stirred overnight (about 15 h). The mixture was quenched with water (6 vol) and stirred for 15 min. Ethyl acetate (EtOAc, 9.000 L, 12 vol) was added and the stirring was continued for 15 min. The stirring was stopped and the mixture was allowed to stand for 10 min, and the aqueous phase was removed. 1 N HCl (6 vol, 4.5 L) was added and stirring was continued for 15 min. The stirring stopped and the aqueous phase was removed. 10% w/v $NaHCO_3$ (4.5 L, 6 vol) was added and the mixture stirred for 10 min. Stirring was stopped and the aqueous phase was removed. Water (6 vol, 4.5 L) was added and the mixture was stirred for 10 min. The aqueous layer was removed, and the organic layer was polish filtered and concentrated to 4 vol. Heptane (5.5 vol, 4 L) was added and the mixture was concentrated again to dryness resulting in 988 g of trans-4-(tert-butoxycarbonylamino)cyclohexylmethanesulfonate.

Method 2.

A three-neck round bottom flask equipped with a mechanical stirrer, addition funnel, nitrogen inlet, thermocouple and drying tube was placed into a cooling tub. Trans-4-(tert-butoxycarbonylamino)cyclohexanol (2599 g, 12.07 mol, 1.0 eq), tetrahydrofuran (THF) (20.8 L), and triethylamine (1466 g, 14.49 mol, 1.2 eq) were added to the flask. The mixture was cooled with an ice water bath and stirred. Methanesulfonyl chloride (1466 g, 12.80 mol, 1.06 eq) was added dropwise by addition funnel over 1 hour. Once the addition was complete, the cooling bath was removed, and the reaction mixture was stirred until TLC indicated the starting material was consumed (about 30 minutes). The reaction mixture was then quenched with an aqueous solution of hydrochloric acid (223 mL of HCl in 6.7 L of water) and EtOAc (10.4 L). The mixture was stirred for approximately 10 to 20 minutes at ambient temperature and then was transferred to a separatory funnel. The layers were separated, and the aqueous layer discarded. The organic layer was washed with water (2×4.5 L), aqueous saturated sodium bicarbonate solution (1×4.5 L), and dried over anhydrous magnesium sulfate with stirring for 5 to 10 minutes. The mixture was filtered and the filter cake was washed with EtOAc (2×600 mL). The combined washes and filtrate were concentrated under reduced pressure at 40° C., leaving a white solid. The solid was taken up in heptane (3 L) and cooled in an ice/methanol cooling tub. More heptane (5 L) was added, and the mixture was stirred at 0 to 5° C. for not less than 1 hour. The solids were then collected by filtration, washed with cold heptane (0 to 5° C., 2×1.3 L), and dried under vacuum at 40° C. to a constant weight to provide the product.

Note: A jacketed reactor may be used instead of a round bottom flask with a cooling tub and ice bath.

Example 1m

Preparation of trans-4-aminocyclohexylmethanesulfonate (C)

Method 1.

Trans-4-(tert-butoxycarbonylamino)cyclohexylmethanesulfonate (985 g, 3.357 mol) was introduced into a 3-neck 12 L flask equipped with a stirrer under a nitrogen atmosphere and open vent. DCM (1.970 L, 2 vol) was added at room temperature, and stirring was commenced. Trifluoroacetic acid (TFA) (2.844 kg, 1.922 L, 24.94 mol, 2 vol) was slowly added to the mixture in two batches of 1 L each. After the first addition, the mixture was stirred for 30 min followed by a second addition. The mixture was stirred overnight (15 h) at room temperature resulting in a clear solution. 2-Methyltetrahydrofuran (4 vol) was then added to the reaction mixture, which was stirred for 1 h. The mixture was then carefully filtered in a fume hood and suction dried to generate 1100 g of TFA salt of trans-4-aminocyclohexylmethanesulfonate with excess TFA.

Method 2.

A 50 L three-neck round bottom flask was equipped with a mechanical stirrer, addition funnel and thermocouple and was placed into a cooling tub. To the flask was added trans-4-(tert-butoxycarbonylamino)cyclohexylmethanesulfonate (3474 g, 1.0 eq) and DCM (5.9 L) to the flask. The resulting suspension was stirred for 5 to 10 minutes at ambient temperature, and then trifluoroacetic acid (TFA, 5.9 L) was added via addition funnel slowly over 2.5 hours to control the resulting exotherm and rate of gas evolution. The reaction mixture was stirred at room temperature overnight and then cooled to 15° C. to 20° C. using an ice water bath. 2-Methyl tetrahydrofuran (2-MeTHF, 11.8 L) was then added via the addition funnel at a rate to maintain the internal temperature below 25° C. (approximately 1.5 hours). The addition of the first 4-5 L of 2-MeTHF was exothermic. The resulting suspension was stirred for 1 hour. The solids were collected by filtration and then washed with 2-MeTHF (2×2.2 L) and then dried under vacuum at ambient temperature to a constant weight to provide the product as a white solid.

Example 1n

Preparation of 7-azabicyclo[2.2.1]heptane hydrochloride (7a)

Method 1.

The TFA salt of trans-4-aminocyclohexylmethanesulfonate (200 g, 650.9 mmol) was introduced into a 3 L, 3-necked flask followed by the addition of water (2.200 L, 11 vol). NaOH (78.11 g, 1.953 mol, 3 eq) was slowly added, keeping the temperature of the reaction mixture below 25° C. and the mixture was stirred overnight. DCM (1.4 L, 7 vol) was then added and the mixture stirred, and the organic layer was separated. The aqueous layer was then extracted a second time with DCM (1.4 L, 7 vol), and the DCM layers were combined. HCl (108.5 mL, 12M, 1.3020 mol, 2 eq) was then added, the mixture was stirred for 30 min and then concentrated on a rotary evaporator to dryness. Acetonitrile (10 vol) was added and the mixture concentrated. This was repeated 3 times until all trace water was azeotropically removed, to provide 7-azabicyclo[2.2.1]heptane hydrochloride (7a). The crude product was recrystallized from acetonitrile (10 vol) to provide 7-azabicyclo[2.2.1]heptane hydrochloride (7a) as a colorless crystalline solid. $^1$HNMR (DMSO-d$^6$) ppm 8.02-8.04 (d); 7.23-7.31 (m); 4.59 (s); 3.31 (s); 2.51-3.3 (m); 1.63-1.75 (m); 1.45-1.62 (m).

As a note, instead of adding DCM for extraction, the crude product can also be distilled at about 95° C. to 97° C. and further recrystallized.

Method 2.

A 50 L three neck round bottom flask equipped with a mechanical stirrer, addition funnel and thermocouple and was placed into a heating mantle. Trans-4-aminocyclohexylmethanesulfonate trifluoroacetate in (3000 g, 1 eq) and water (30 L) were added to the flask. The mixture was stirred, as 50% NaOH (2343 g, 29.29 mol, 3 eq) was added by an addition funnel at such a rate as to maintain the temperature below 25° C. because the addition was mildly exothermic. Upon completion of the NaOH addition, the reaction mixture was stirred overnight at room temperature. The product was recovered by fractional distillation at reflux temperature, (approximately 100° C.) with a head temperature of 95 to 98° C.

The pH of each fraction was adjusted to 2 by adding HCl, and concentrated under reduced pressure at 55° C. to leave a thick paste. Acetonitrile (ACN 1.5 L) was added and the resulting suspension was stirred for 30 minutes and then cooled to 0 to 5° C. for 1 hour. The solids were collected by filtration, washed with cold (0 to 5° C.) ACN (2×600 mL), and dried under vacuum at 50° C. to a constant weight.

A 22 L three-neck round bottom flask was equipped with a mechanical stirrer, thermocouple, and condenser and placed into a heating mantle. The collected solids (2382 g), methanol (4.7 L) and 2-MeTHF (4.7 L) were added to the flask. The resulting suspension was stirred and heated to reflux (approximately 65° C.). The reaction flask was transferred to a cooling tub, and the mixture was stirred. 2-MeTHF (4.7 L) was then added via addition funnel over 30 minutes. The resulting suspension was cooled to 0 to 5° C. and stirred at this temperature for 30 minutes. The solids were collected by filtration, washed with cold (0 to 5° C.) 2-MeTHF (2×600 mL), and then dried under vacuum at 55° C. to a constant weight.

A 12 L three-neck round bottom flask equipped with a mechanical stirrer, thermocouple, nitrogen inlet and condenser was placed into a heating mantle. The crude product (2079 g) and ACN (6.2 L) were added to the flask. The resulting suspension was stirred and heated to reflux (approximately 82° C.) for 30 minutes. The flask was transferred to a cooling tub and the suspension was slowly cooled to 0 to 5° C. and maintained at this temperature for 1 hour. The solids were collected by filtration, washed with cold (0 to 5° C.) ACN (3×600 mL), and dried under vacuum at 55° C. to a constant weight affording to provide the product.

Example 2

Preparation of Compounds of Formula I by Biotransformation

Reagents and Materials

The clone of BM3-M11 mutant was obtained from the Vrije University, Amsterdam. The BM3-P450 enzyme was expressed in *E. coli* and prepared by fermentation. Whole-cell lysate was used in metabolite preparation. The following reagents were obtained from Sigma Aldrich: (1) NADP$^+$ (β-Nicotinamide adenine dinucleotide phosphate sodium salt hydrate); (2) G6P (D-Glucose 6-phosphate sodium salt); (3) G6PDH (Glucose-6-phosphate Dehydrogenase from baker's yeast); and (4) Potassium phosphate buffer salt. Strata $C_{18}$ reversed-phase solid-phase extraction cartridges were obtained from Phenomenex.

Biosynthetic Preparation

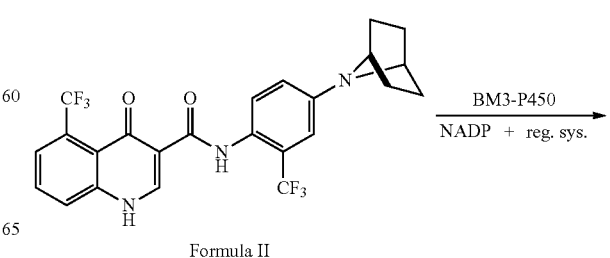

Formula II

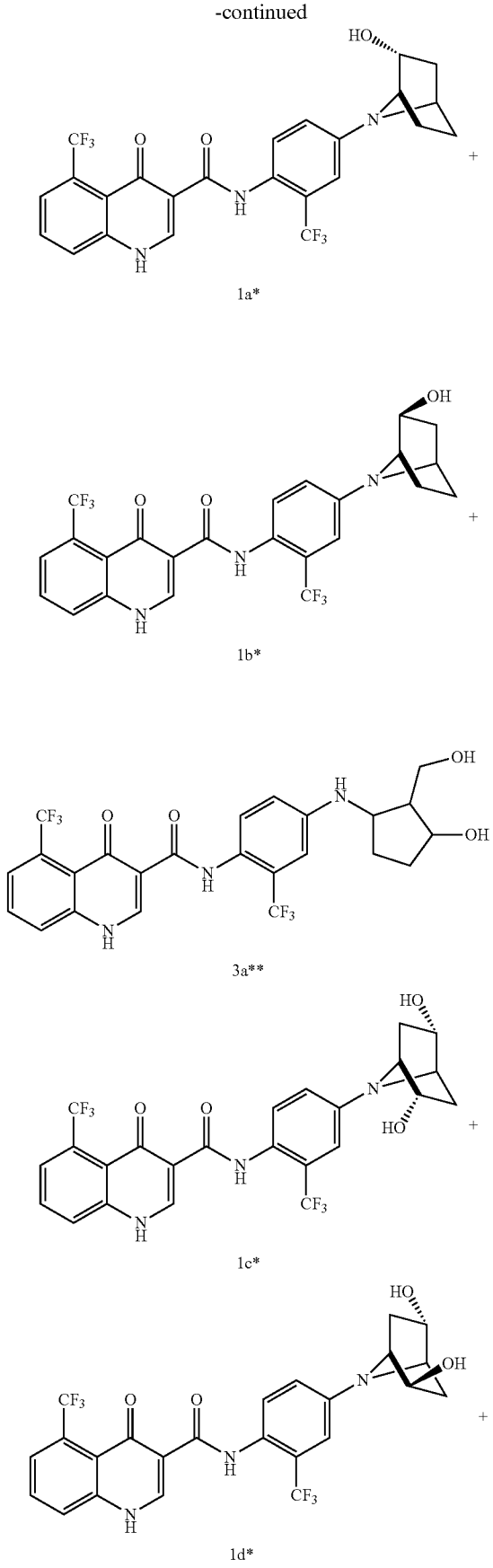
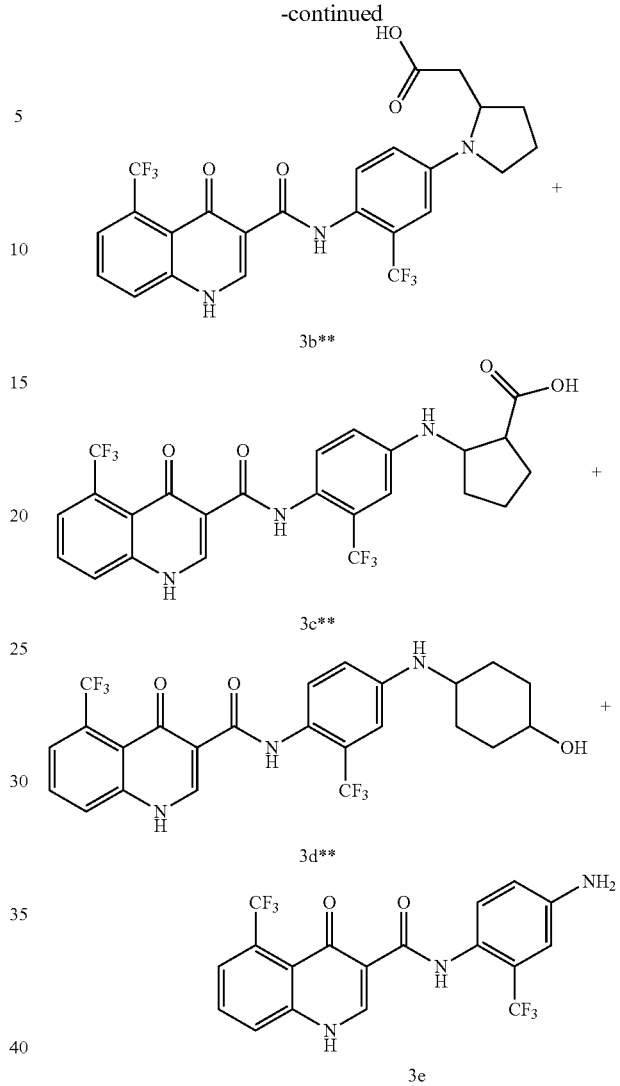

*Note: Compounds 1a-1d are each drawn as a single enantiomer, but are meant to include all possible stereoisomers.
**Further Note: Compounds 3a-3d are each drawn with non-specific stereochemistry and are meant to include all possible stereoisomers.

Method 1

A 200 mL batch of incubation mixture was prepared as follows. To a glass bottle, add 130 ml of 0.1M pH 7.4 potassium phosphate buffer, 10 mL of 0.1M G6P, 10 mL of 40 mM $NADP^+$, 20 mL of 0.3 mM $MgCl_2$, 20 mL of 0.1 μM BM3-M11, 8 mL of 10 mM DMSO stock solution of the Compound of Formula II, and 2 mL of 100 U/mL G6PDH. The solution was mixed thoroughly and incubated at 23° C. on a shaking water bath for 22 hr. The reaction was quenched with 200 mL of cold methanol followed by centrifugation at 4000 rpm for 15 min. The supernatant was collected and methanol was removed by rotary evaporation. The resulting aqueous solution was passed through a 10 g $C_{18}$ solid-phase extraction cartridge. Retained substances were eluted with two portions of 10 mL acetonitrile. The crude extract was dried and solid residue was dissolved in 8 mL of DMSO for HPLC purification.

Method 2

A 2 L batch of incubation mixture was prepared according to the following procedure. In an appropriately sized glass container, 1300 mL of 0.1 M pH 7.4 potassium phosphate buffer, 100 mL of 0.1 M G6P, 100 mL of 40 mM NADP$^+$, 200 mL of 0.3 mM MgCl$_2$, 200 mL of 1 μM BM3-M11, 80 mL of 10 mM DMSO stock solution of the Compound of Formula II, and 20 mL of 100 U/mL G6PDH were mixed. The solution was divided into five 400 mL portions in 1 L bottles, incubated at 24° C. on a shaking water bath for 22 hr. The reaction was quenched with 2000 mL of cold methanol followed by centrifugation at 4000 rpm for 15 min.

Purification and Separation of Products.

Method 1.

The resulting mixture of compounds of Formula I were purified by reversed-phase HPLC, with a Phenomenex Luna C8(2) column (50 mm×21 mm I.D., 5 μm, 100 Å). Mobile phases were water (A) and acetonitrile (B), gradient from 30% B to 37% B in 12 min at 25 mL/min, 310 nm UV detection, 1 mL injection. Fractions corresponding to the two monohydroxy products were collected and dried by rotary evaporation. The exo and endo isomer structures of the mixture of compounds of Formula I were determined by NMR.

Chiral separations of the enantiomeric pair of Endo and Exo compounds of Formula I were performed on two 2-dimensional achiral-chiral LC-MS/MS methods, respectively. The mixture of compounds of Formula I were separated in to Endo and Exo isomers in the first dimension using a reverse-phase column, followed by further separation into four single enantiomers in the second dimension using two different chiral columns.

1. Separation of Endo Compounds of Formula I

LC Conditions

Column: Luna C8(2) 2.00×30 mm, 3 μm particle size (Phenomenex) and OD-RH 2.1×150 mm, 5 μm particle size (Chiral Technologies)

Mobile Phase: ACN/water; 0.45 ml/min, 0-8 min: 33% ACN, 8.1-19 min: 40% ACN, 19.1-25 min: 33% ACN MS Transition:

512/240

2. Separation of Exo Compounds of Formula I

LC Conditions

Column: Luna C8(2) 2.00×30 mm, 3 μm particle size (Phenomenex) and OJ-RH 2.1×150 mm, 5 μm particle size (Chiral Technologies)

Mobile Phase: ACN/water; 0.45 ml/min; 0-6 min: 33% ACN, 6.1-15 min: 45% ACN, 15.1-18 min: 33% ACN MS Transition:

512/240 or 512/466

Method 2.

The products of the biotransformation were analyzed by HPLC, with a Synergi MAX-RP, 150×2 mm I.D, 80 Å, 2.5 μm column. Mobile phases were 0.05% formic acid in water (Mobile Phase A) and 0.05% formic acid in acetonitrile (Mobile Phase B). Gradients were 40% B-50% B-95% B at 0 min-25 min-30 min, at a 0.3 mL/min flow rate with 300 nm UV detection at room temperature.

Method 3.

The products of the biotransformation were analyzed by HPLC, with a Synergi MAX-RP, 150×2 mm I.D, 80 Å, 2.5 μm column. Mobile phases were 0.05% formic acid in water (Mobile Phase A) and 0.05% formic acid in acetonitrile (Mobile Phase B). Gradients were 5% B-60% B-95% B at 0 min-15 min-20 min, at a 0.5 mL/min flow rate.

The retention times provided in Table 1 were determined using HPLC Method 3. Alternatively, the products of the biotransformation can be separated and isolated using Methods 1 or 2 as described above.

TABLE 1

Characterization of selected compounds

| Compound | $^1$H NMR Data; 500 MHz; DMSO-d$_6$ | MS (M + H) | Retention Time (min); [relative to Formula II] |
|---|---|---|---|
| Formula II | NMR characterization is provided above. | 496 | 17.33; [1.00] |
| 1a* | δ 1.25 (d, J = 7.9 Hz,), 1.47 (m,), 1.53 (m, ), 1.55 (m,), 1.81 (dd, J = 12.3, 7.6 Hz), 3.77 (d, J = 6.8 Hz,), 4.09 (d, J = 3.8 Hz,), 4.32 (bs), 7.10 (s), 7.16 (d, J = 8.8 Hz,), 7.71 (t, J = 8.2 Hz,), 7.77 (d, J = 8.3 Hz,), 7.90 (d, J = 8.8 Hz,), 7.97 (d, J = 8.1 Hz,), 8.89 (s), 12.87 (s). | 512 | 14.63; [0.84] |
| 1b* | δ 1.03 (d, J = 13.0 Hz,), 1.46 (m), 1.61(m), 2.11 (m), 4.15 (m), 4.17 (bd, J = 4.4 Hz,), 4.22 (bt), 7.08 (s), 7.16 (d, J = 8.8 Hz,), 7.66 (t, J = 7.5 Hz,), 7.72 (d, J = 7.3 Hz,), 7.92 (d, J = 8.7 Hz,), 7.96 (d, J = 7.8 Hz,), 8.88 (s), 13.05 (s). | 512 | 14.41; [0.83] |
| 1c* | δ 0.86 (dd, J = 12.7, 3.4 Hz, 1H), 1.39 (dd, J = 11.9, 5.3 Hz, 1H), 2.01 (m, 1H), 2.46 (dd, J = 12.7, 7.3 Hz, 1H), 3.85 (d, J = 7.0 Hz, 1H), 3.95 (m, 1H), 4.03 (d, J = 5.4 Hz, 1H), 4.19 (t, J = 4.5 Hz, 1H), 7.08 (s, 1H), 7.13 (d, J = 8.8 Hz, 1H), 7.82 (m, 1H), 7.84 (m, 1H), 7.85 (m, 1H), 8.00 (d, J = 8.0 Hz, 1H), 8.87 (s, 1H), 12.46 (s, 1H). | 528 | 12.47; [0.72] |
| 1d* | δ 1.39 (m, 2H), 1.65 (dd, J = 12.8, 7.0 Hz, 1H), 3.74 (m, 2H), 4.19 (d, J = 5.0 Hz, 2H), 7.09 (s, 1H), 7.12 (d, J = 8.8 Hz, 1H), 7.72 (m, 1H), 7.74 (m, 1H), 7.77 (m, 1H), 8.35 (m, 1H), 8.88 (s, 1H), 12.48 (bs, 1H). | 528 | 12.23; [0.71] |
| 3a** | δ 1.15 (m, 1H), 1.62 (dt, J = 13.0, 6.8 Hz, 1H), 1.86 (m, 1H), 1.89 (m, 1H), 2.27 (dt, J = 13.7, 7.6 Hz, 1H), 3.35 (m, 1H), 3.47 (m, 1H), 3.84 (m, 1H), 3.93 (m, 5.97 (bs, 1H), 6.76 (d, J = 9.2 Hz, 1H), 6.83 (s, 1H), 7.69 | 528 | 12.63; [0.73] |

TABLE 1-continued

Characterization of selected compounds

| Compound | $^1$H NMR Data; 500 MHz; DMSO-$d_6$ | MS (M + H) | Retention Time (min); [relative to Formula II] |
|---|---|---|---|
| | (m, 2H), 7.69 (m, 2H), 7.73 (m, 1H), 7.95 (m, 1H), 8.86 (s, 1H), 12.84 (s, 1H). | | |
| 3b** | δ 1.55 (m, 1H), 1.78 (m, 1H), 1.87 (m, 1H), 2.27 (m, 1H), 2.45 (ddd, J = 16.3, 9.6, 5.3 Hz, 1H), 2.60 (dt, J = 17.1, 8.6 Hz, 1H), 3.47 (t, J = 6.4 Hz, 2H), 4.47 (m, 1H), 7.71 (dd, J = 8.7, 2.5 Hz, 1H), 7.86 (m, 1H), 7.89 (m, 1H), 7.99 (d, J = 2.5 Hz, 1H), 8.02 (d, J = 2.5 Hz, 1H), 8.35 (d, J = 8.9 Hz, 1H), 8.92 (s, 1H), 12.84 (s, 1H). | 528 | 12.93; [0.75] |
| 3c** | δ 1.51 (m, 1H), 1.72 (m, 1H), 1.75 (m, 1H), 1.98 (m, 1H), 2.05 (m, 1H), 2.11 (m, 1H), 2.86 (m, 1H), 3.84 (m, 1H), 6.04 (bs, 1H), 6.80 (d, J = 9.1 Hz, 1H), 6.83 (s, 1H), 7.71 (m, 2H), 7.71 (m, 2H), 7.76 (m, 2H), 7.98 (d, J = 8.1 Hz, 1H), 8.86 (s, 1H), 12.84 (s, 1H). | 530 | 14.73; [0.85] |
| 3d** | δ 1.30 (m, 2H), 1.79 (m, 2H), 2.19 (m, 2H), 2.54 (m, 2H), 3.32 (d, J = 6.5 Hz, 2H), 3.75 (m, 1H), 5.92 (s, 1H), 6.78 (d, J = 8.9 Hz, 1H), 6.83 (s, 1H), 7.63 (t, J = 7.6 Hz, 1H), 7.70 (d, J = 8.5 Hz, 2H), 7.70 (d, J = 8.5 Hz, 2H), 7.96 (d, J = 8.4 Hz, 1H), 8.87 (s, 1H), 12.85 (s, 1H). | 514 | 14.62; [0.84] |
| 3e | δ 6.81 (d, J = 8.6 Hz, 1H), 6.91 (s, 1H), 7.62 (d, J = 8.6 Hz, 1H), 7.82 (m, 2H), 7.82 (m, 2H), 8.25 (d, J = 9.0 Hz, 1H), 8.88 (s, 1H), 12.23 (s, 1H). | 416 | 13.72; [0.79] |

*Note: Compounds 1a-1d are each drawn as a single enantiomer, but are meant to include all possible stereoisomers.
**Further Note: Compounds 3a-3d are each drawn with non-specific stereochemistry and are meant to include all possible stereoisomers.

Example 3

Organic Solvent Effects on Product Yield of Biotransformation

The studies were performed in triplicates under this method with total incubation volume of 600 μL. Final concentrations of the incubation solutions were pH 7.4 buffer of 0.05 M potassium phosphate and 0.05 M potassium chloride; 0.5 mM NADP$^+$; 2 mM G6P; 0.5 U/mL G6PDH; 100 μM Mg$^{2+}$; and 4% DMSO. The final concentrations of the compounds of Formula II and P450 from BM3-M11 were 16 μM and 200 nM respectively. Three cosolvents, DMSO, ACN, and MeOH, were each added to the incubation solution to study their effect on product yield with BM3-P450 biotransformation. Cosolvent composition was varied as % (v/v) at 1, 4, 8, 12, 16, 20, 25, 40. Solutions were incubated at 24° C. in a shaking water bath for 90 min. Incubation was quenched with 1:1 volume of cold ACN, followed by centrifugation. Supernatant was used for HPLC/MS/UV analysis. Quantification of parent depletion was monitored by MRM with API-365/EP10 mass spectrometer. Product formation was measured by HPLC-UV/MS, on an LTQ mass spectrometer with electrospray interface, and a UV detector set at 300 nm. Separation and purification of the products is described above.

Example 4

Organic Solvent Effects on the Kinetic Parameters of Biotransformation

Michaelis Menten enzyme kinetics parameters at 0 and 20% (v/v) methanol were determined by measuring the product formation with a UV detector at 300 nm, using compound of Formula II as the reference standard. Concentrations (μM) of compounds of Formula II (starting materials) were varied at 5, 8, 10, 15, 20, 25, 50 and 80. Studies were performed in triplicates at 1 mL total incubation volume. Four time points, 0 min, 10 min, 20 min, 30 min were measured. Final concentration of solution components were 1% (v/v) DMSO; 100 nM BM3-M11; 50 mM tris-buffer at pH 7.5; 0.5 mM NADP$^+$; 2 mM G6P and 0.5 U/mL G6PDH. Solutions were quenched with 1:1 volume of cold ACN, centrifuged and supernatant was used for analysis.

Example 5

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl⁻ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, $CaCl_2$ 2, $MgCl_2$ 1, HEPES 10, pH 7.4 with NaOH.

Chloride-Free Bath Solution: Chloride Salts in Bath Solution #1 are Substituted with Gluconate Salts.

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

Electrophysiological Assays for assaying ΔF508-CFTR modulation properties of compounds.

Using Chamber Assay

Using chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, Iowa). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$, 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 μM) and all test compounds were added to the apical side of the cell culture inserts. The efficacy of the putative ΔF508-CFTR potentiators was compared to that of the known potentiator, genistein.

Patch-Clamp Recordings

Total Cl⁻ current in ΔF508-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 $CaCl_2$, 10 EGTA, 10 HEPES, and 240 μg/mL amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, 1× pen/strep, and 25 mM HEPES in 175 $cm^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≦2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Examples of activities and efficacies of the compounds of Formula I are shown below in Table 2. The compound activity is illustrated with "+++" if activity was measured to be less than 2.0 µM, "++" if activity was measured to be from 2 µM to 5.0 µM, "+" if activity was measured to be greater than 5.0 µM, and "-" if no data was available. The efficacy is illustrated with "+++" if efficacy was calculated to be greater than 100%, "++" if efficacy was calculated to be from 100% to 25%, "+" if efficacy was calculated to be less than 25%, and "-" if no data was available. It should be noted that 100% efficacy is the maximum response obtained with 4-methyl-2-(5-phenyl-1H-pyrazol-3-yl)phenol.

TABLE 2

| Compound No. | Activity $EC_{50}$ (µm) | % Efficacy |
|---|---|---|
| Formula II | +++ | ++ |
| 1a | +++ | ++ |
| 1b | +++ | +++ |

Some compounds described herein, for example Compounds 1c, 1d, 3a, 3b, 3c, 3d and 3e, are useful as analytical tools for determining the products and biproducts of biological transformations such as those described herein.

What is claimed is:

1. A method of producing the compounds of Formula I:

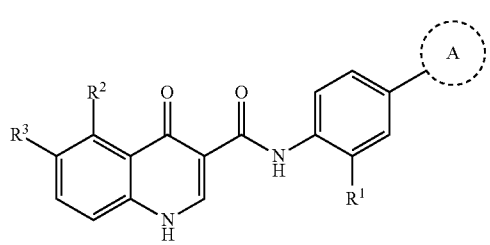

or pharmaceutically acceptable salts thereof, wherein $R^1$ is $—CF_3$, $R^2$ is $—CF_3$, $R^3$ is H, and ring A is selected from

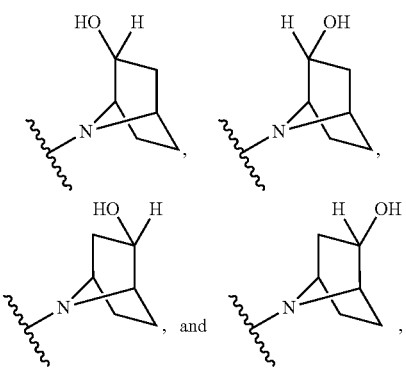

comprising contacting the compound of Formula II with a CYP-102 enzyme, BM3-M11, to produce a mixture of compounds of Formula I, wherein the compound of Formula II has the structure

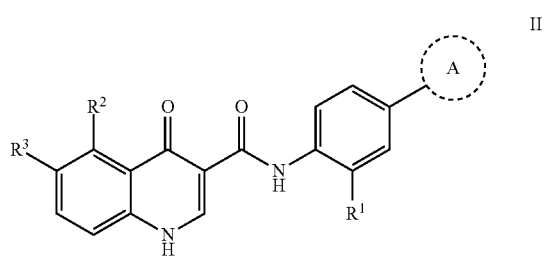

in which $R^1$ is $—CF_3$, $R^2$ is $—CF_3$, $R^3$ is H, and ring A is

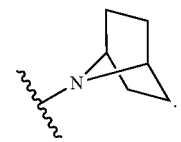 [SMILES: *N1C2CCC1CC2]

2. The method of claim 1, wherein the process is optionally conducted in the presence of an organic solvent.

3. The method of claim 2, wherein the solvent is acetonitrile, methanol, acetone, dimethylsulfoxide, and dimethylformamide or mixtures thereof.

4. The method of claim 3, wherein the process is conducted in the presence of methanol.

5. The method of claim 2, wherein the organic solvent is present in an amount of less than about 30% (v/v).

6. The method of claim 5, wherein the organic solvent is present in an amount of less than about 25% (v/v).

7. The method of claim 5, wherein the organic solvent is present in an amount of less than or equal to about 20% (v/v).

8. The method of claim 2, wherein the organic solvent is present in an amount of between about 5% to about 25% (v/v).

9. The method of claim 8, wherein the organic solvent is present in an amount of between about 10% to about 20% (v/v).

10. The method of claim 1, further comprising separating the mixture of compounds of Formula I.

11. The method of claim 10, wherein the Exo and Endo isomers and each of their enantiomeric pairs of present in the mixture of compounds of Formula I are separated by chiral LC-MS/MS.

12. The method of claim 11, wherein ring A of the separated isomer of Formula I is

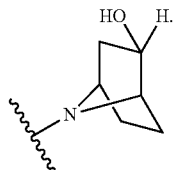

13. The method of claim 11, wherein ring A of the separated isomer of Formula I is

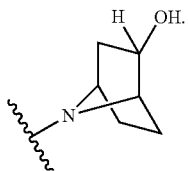 [SMILES: *N1C2CCC1C(O)C2]

14. The method of claim 11, wherein ring A of the separated isomer of Formula I is

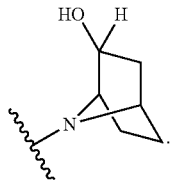 [SMILES: *N1C2CCC1C(O)C2]

15. The method of claim 11, wherein ring A of the separated isomer of Formula I is

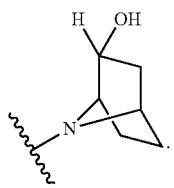 [SMILES: *N1C2CCC1C(O)C2]

* * * * *

UNITED STATES PATENT AND TRADEMARK OFFICE
CERTIFICATE OF CORRECTION

PATENT NO. : 8,404,849 B2  
APPLICATION NO. : 13/112868  
DATED : March 26, 2013  
INVENTOR(S) : Lifang Sun et al.

Page 1 of 1

It is certified that error appears in the above-identified patent and that said Letters Patent is hereby corrected as shown below:

Title Page:
Item (73) Assignee should read: Vertex Pharmaceuticals Incorporated, Cambridge, MA (US)

Signed and Sealed this
Eighth Day of October, 2013

Teresa Stanek Rea
*Deputy Director of the United States Patent and Trademark Office*